(12) United States Patent
Skudas et al.

(10) Patent No.: US 12,358,944 B2
(45) Date of Patent: Jul. 15, 2025

(54) GLYCOFORM PURIFICATION

(71) Applicant: Merck Patent GmbH, Darmstadt (DE)

(72) Inventors: Romas Skudas, Mainz (DE); Annika Holzgreve, Seligenstadt (DE); Alisa Strobel, Mannheim (DE)

( * ) Notice: Subject to any disclaimer, the term of this patent is extended or adjusted under 35 U.S.C. 154(b) by 866 days.

(21) Appl. No.: 17/623,914

(22) PCT Filed: Jul. 1, 2020

(86) PCT No.: PCT/EP2020/068439
§ 371 (c)(1),
(2) Date: Dec. 30, 2021

(87) PCT Pub. No.: WO2021/001388
PCT Pub. Date: Jan. 7, 2021

(65) Prior Publication Data
US 2022/0380406 A1  Dec. 1, 2022

(30) Foreign Application Priority Data

Jul. 3, 2019 (EP) ..................................... 19184130
Apr. 30, 2020 (EP) ..................................... 20172272

(51) Int. Cl.
| | |
|---|---|
| *C07K 1/18* | (2006.01) |
| *B01D 15/36* | (2006.01) |
| *B01J 20/288* | (2006.01) |
| *B01J 20/32* | (2006.01) |
| *B01J 43/00* | (2006.01) |
| *C07K 16/06* | (2006.01) |

(52) U.S. Cl.
CPC .............. *C07K 1/18* (2013.01); *B01D 15/361* (2013.01); *B01J 20/288* (2013.01); *B01J 20/321* (2013.01); *B01J 20/3276* (2013.01); *B01J 20/3278* (2013.01); *B01J 43/00* (2013.01); *C07K 16/065* (2013.01); *C07K 2317/41* (2013.01)

(58) Field of Classification Search
None
See application file for complete search history.

(56) References Cited

U.S. PATENT DOCUMENTS

| | | |
|---|---|---|
| 4,568,706 A | 2/1986 | Noetzel et al. |
| 5,453,186 A | 9/1995 | Muller et al. |
| 6,143,853 A | 11/2000 | Ericsson et al. |
| 8,765,897 B2 | 7/2014 | Joehnck et al. |
| 2002/0164328 A1 | 11/2002 | Shinkawa et al. |

(Continued)

FOREIGN PATENT DOCUMENTS

| | | |
|---|---|---|
| CN | 101678318 A | 3/2010 |
| CN | 103827134 A | 5/2014 |

(Continued)

OTHER PUBLICATIONS

Kullolli et al. (Journal of Separation Science, 2008, 31, 2733-2739). (Year: 2008).*

(Continued)

*Primary Examiner* — Clare M Perrin
(74) *Attorney, Agent, or Firm* — EMD Millipore Corporation

(57) ABSTRACT

The present invention relates to a method for the separation and purification of glycoforms with an ion exchange separation material with amino-acid based endgroups.

13 Claims, 14 Drawing Sheets

(56) References Cited

U.S. PATENT DOCUMENTS

| | | | | |
|---|---|---|---|---|
| 2008/0253992 | A1* | 10/2008 | DeFrees | C07K 1/13 435/68.1 |
| 2010/0151584 | A1 | 6/2010 | Parsons et al. | |
| 2010/0181254 | A1 | 7/2010 | Graalfs | |
| 2013/0084648 | A1* | 4/2013 | Bolton | C12P 21/005 530/391.1 |
| 2013/0193051 | A1* | 8/2013 | Wirth | G01N 30/56 100/35 |
| 2015/0361128 | A1* | 12/2015 | Rajendran | C07K 16/22 530/388.1 |
| 2017/0129963 | A1 | 5/2017 | Bhakta et al. | |
| 2019/0056360 | A1* | 2/2019 | Lauber | B01J 20/3212 |
| 2019/0119415 | A1 | 4/2019 | Graalfs | |
| 2019/0367556 | A1 | 12/2019 | Nadkarni et al. | |
| 2020/0002391 | A1* | 1/2020 | Knaupp | B01D 15/3804 |
| 2020/0017544 | A1* | 1/2020 | Rosenberg | C07K 1/16 |

FOREIGN PATENT DOCUMENTS

| | | | |
|---|---|---|---|
| CN | 105229498 | A | 1/2016 |
| CN | 104208719 | B | 5/2017 |
| CN | 108314729 | A | 7/2018 |
| EP | 0129719 | B1 | 11/1988 |
| EP | 0337144 | B1 | 5/1992 |
| JP | 2010528271 | A | 8/2010 |
| JP | 2016504337 | A | 2/2016 |
| TW | 201113281 | A1 | 4/2011 |
| WO | 9513861 | A1 | 5/1995 |
| WO | 07014591 | A1 | 2/2007 |
| WO | 11139985 | A1 | 11/2011 |
| WO | 14100117 | A2 | 6/2014 |
| WO | 17109619 | A1 | 6/2017 |
| WO | 21001388 | A1 | 1/2021 |

OTHER PUBLICATIONS

Kozlik et al. (Anal Bioanal Chem., 2018, 410(20), 5001-5008). (Year: 2018).*

Li et al. (Journal of Chromatography A, 2015, 1404, 51-59). (Year: 2015).*

Totten et al. (Nature Scientific Reports, 2018, 8, 6509). (Year: 2018).*

Office Action dated May 31, 2024 issued in corresponding TW 109122457 application (6 pages).

Durocher Ybutler M: "Expression systems for therapeutic glycoprotein production", Curr Opin Biotechnol, vol. 20, 2009, pp. 700-707, XP026778881, DOI: 10.1016/j.copbio.2009.10.008.

Fangj. Richardson Jdu Zzhang Z: "Effect of Fc-Glycan Structure on the Conformational Stability of IgG Revealed by Hydrogen/Deuterium Exchange and Limited Proteolysis", Biochemistry, vol. 55, 2016, pp. 860-868.

Rodrigues ME, Henriques M, Oliveira R, Azeredo J. Glycosylation: impact, control and improvement during therapeutic protein production, Crit Rev Biotechnol. 2013, 1-19.

Goetze Amliu Ydzhang Zshah Blee Ebondarenko PVFLYNN GC: "High mannose glycans on the Fc region of therapeutic IgG antibodies increase serum clearance in humans", Glycobiology, vol. 21, 2011, pp. 949-959, XP002736310, DOI: 10.1093/glycob/cwr027.

Raju TS: "Terminal sugars of Fc glycans influence antibody effector functions of IgGs", Curr Opin Immunol, vol. 20, 2008, pp. 471-478, XP025771206, DOI: 10.1016/j.coi.2008.06.007.

Peipp et al.: "Antibody fucosylation differentially impacts cytotoxicity mediated by NK and PMN effector cells", Blood, vol. 112, No. 6, Sep. 15, 2008 (Sep. 15, 2008), pp. 2390-2399, XP055117231, DOI: 10.1182/blood-2008-03-144600.

Liu L: "Antibody Glycosylation and Its Impact on the Pharmacokinetics and Pharmacodynamics of Monoclonal Antibodies and FC-Fusion Proteins", Journal of Pharmaceutical Sciences, vol. 104, 2015, pp. 1866-1884, XP055295176, DOI: 10.1002/jps.24444.

Buffers. A Guide for the Preparation and Use of Buffers in Biological Systems, Gueffroy, D., ed. Calbiochem Corporation (1975) (pp. 1-39).

Ôi N, Kitahara H. Enantiomer separation by HPLC with some urea derivatives of L-valine as novel chiral stationary phases. Journal of liquid chromatography. Feb. 1, 1986;9(2-3):511-7.

Meng Ruan et al: "Preparation and evaluation of tert-leucine derivative functionalized polymeric monoliths for micro-liquid chromatography", Electrophoresis, vol. 38, No. 22-23, Nov. 1, 2017 (Nov. 1, 2017), pp. 3020 3028, XP055727663, Issn: 0173-0835, DOI: 10.1002/elps.201700176.

Fu Dongmei et al: "Preparation of glutathione-functionalized zwitterionic silica material for efficient enrichment of sialylated N-glycopeptides", Coresta PTM Technical Report, Springer Berlin Heidelberg, DE, vol. 411, No. 18, Mar. 4, 2019 (Mar. 4, 2019), pp. 4131-4140, XP036820245, ISSN: 1618-2642, [retrieved on 20190304], DOI: 10.1007/S00216-019-01661-0.

International Search Report PCT/EP2020/058439 dated Oct. 15, 2020. (pp. 1-4).

* cited by examiner

GLYCOFORM PURIFICATION

The present invention relates to a method for the separation and purification of glycoforms with an ion exchange separation material with amino-acid based endgroups.

Glycans are an essential part from glycoprotein molecules, assuring its structure and function.

One of the most common glycoproteins are immunoglobulins containing two N-linked oligosaccharides at the conserved Asparagine 297 in the CH2 domain of the Fc part. The structure of the glycan is composed of two N-acetylglucosamine (GlcNAc), three mannose and two GlcNAc residues. Additional monosaccharides such as fucose (Fuc), galactose (Gal), sialic acid including N-acetylneuraminic acid (NANA) or N-glycolylneuraminic acid (NGNA) residues can be present as well. (FIG. 1. Glycan structure). The glycan structure plays an important role for the glycoprotein and receptor affinity binding. Change of glycan composition can cause conformation transformation of the glycoprotein, influencing its specific receptor binding and resulting in changes of effector functions. Moreover, some glycan compositions initiate protective organism reactions, e.g. terminal mannose binding to mannose binding receptor (ManR) carrying effectors.

Besides, high terminal mannose glycan containing glycoproteins, commonly found in glycoproteins derived from yeasts, insect cells and plants, could be highly immunogenic in humans (Durocher Y, Butler M. 2009. Expression systems for therapeutic glycoprotein production. Curr Opin Biotechnol 20: 700-707). Therefore, it is very important to control the level of high terminal mannose glycans in the biopharmaceutical glycoprotein to avoid potential immunogenicity.

Furthermore, terminal mannose and hybrid glycan structures decrease the conformational stability of the monoclonal antibody (mAb) CH2 domain. This may cause higher level of enzymatic degradation or short storage time for such molecules (Fang, J. Richardson J, Du Z, Zhang Z. Effect of Fc-Glycan Structure on the Conformational Stability of IgG Revealed by Hydrogen/Deuterium Exchange and Limited Proteolysis, Biochemistry 2016, 55, 860-868).

Hybrid glycosylation variants are often formed in the Golgi apparatus. Hybrid glycosylation variants show reduced or altered glycosylation, in other words do not have the desired glycosylation pattern. Some examples of hybrid forms include variants lacking N-acetylglucosamine in G0 variant (e.g. G0-N) or lacking of Galactose in G1 variant (e.g. G1-N) (Costa A R, Rodrigues M E, Henriques M, Oliveira R, Azeredo J. Glycosylation: impact, control and improvement during therapeutic protein production, Crit Rev Biotechnol. 2013, 1-19). Both mentioned hybrid variants have a terminal mannose, thereby increasing the probability of shorter lifetime in blood (Goetze A M, Liu Y D, Zhang Z, Shah B, Lee E, Bondarenko P V, Flynn G C. 2011. High mannose glycans on the Fc region of therapeutic IgG antibodies increase serum clearance in humans. Glycobiology 21: 949-959).

Moreover, lower levels of galactose reduce the complement-dependent cytotoxic (CDC) activity, influencing the glycoprotein activity. Several studies have shown, that the activity can be reduced two-fold, between mAbs containing G2-glycoforms and mAbs containing G0-glycoforms (Raju T S. 2008. Terminal sugars of Fc glycans influence antibody effector functions of IgGs. Curr Opin Immunol 20: 471-478). Therefore, an ability to control or reduce the amount of the hybrid glycosylation variants, especially the ones with terminal mannose or lacking galactose would increase the lifetime and efficacy of the glycoprotein.

One of the most evident effect of glycan structure changes is seen by the presence or lack of fucose. Fucose is added to the glycan structure in the Golgi apparatus. It is known that the presence of fucose in core glycan structure of a mAb will inhibit its binding to FcγRIIIa receptors, thus decreasing antibody-dependent cell-mediated cytotoxicity (ADCC) activity.

The specific binding to the FcγRIIIa receptor can be decreased 50-fold, thereby having a great effect on the efficacy of the glycoprotein (Peipp et al, Antibody fucosylation differentially impacts cytotoxicity mediated by NK and PMN effector cells, BLOOD, 15 Sep. 2008, Volume 112, Number 6, 2390-2399).

It is also well known, that the absence of glycosylation dramatically reduces the binding affinity between glycoprotein and the receptor. For example, the lack of glycosylation on mAbs dramatically reduces the binding to FcγRI receptors and eliminates the binding to FcγRII and FcγRIII receptors (Liu L, Antibody Glycosylation and Its Impact on the Pharmacokinetics and Pharmacodynamics of Monoclonal Antibodies and FC-Fusion Proteins, Journal of Pharmaceutical Sciences 104: 1866-1884, 2015).

The Food and Drug administration (FDA) rates glycosylation similarities for biosimilar drugs as one of the most critical requirements (FDA, 2012. Guidance for industry quality considerations in demonstrating biosimilarity to a reference protein product). Moreover, glycosylation enhancement is one of the main tendencies for the biobetters.

For all those reasons, there is an increasing need in the industry to enhance the efficiency of glycosylated biopharmaceutical molecules by controlling, enriching or separating various glycan species and enabling the best pharmacokinetics, efficacy, half-life, and tolerability.

The current state-of-art for glycoprotein separation based on its glycan variants can be performed in preparative chromatography mode enriching high mannose glycoforms using ion exchange chromatography (WO 2014/100117). Unfortunately, the enrichment of the high mannose containing glycoforms in given examples overlaps with aggregate enrichment, making it hard to recognize, if no aggregate containing glycoprotein separation will be achieved as well. Moreover, there is no indication, that this technology can be used for other glycan variant separation or removal.

An alternative technology for the high mannose containing glycoforms is affinity chromatography using lectins (US 20020164328). Though this technology is more specific as the ion exchange chromatography, it is limited to the high mannose containing glycans and specific binding conditions are required. Additionally, the leaching of lectin, regeneration and lifetime of this resin hinders its application in economic high mannose containing glycan variant separations.

Other preparative glycan variant separation methods include a combination of anion exchange and reversed phase chromatography techniques (US 20100151584) or using only anion exchange chromatography (IN 01066ch2012). Unfortunately, none of the prior-art technologies achieve more than one glycoform separation, corresponding to the clear need of an efficient and effective technique to separate the glycoforms of the glycoprotein.

It has been found that an ion exchange material carrying covalently attached leucine residues or similar residues can be used for the separation and enrichment of glycoforms enabling an efficient glycan species separation at >10 mg glycoprotein/ml material capacities. In a more preferred embodiment the capacity is between 10-80 mg/ml. Moreover, this innovative ion exchange material can be used in high conductivity>10 mS/cm, where in more preferred embodiment the conductivity is between 10-60 mS/cm. Surprisingly, it was possible to separate and enrich glycan variants including high mannose containing variants, terminal mannose containing variants, fucose containing variants and no glycosylation containing variants using a solvent pH gradient. Moreover, this discovery enabled us to explore a broad window of operation, where the ionic and hydrophobic interaction contributed to the selectivity of glycan variant separation. Additionally, the application of this innovative ion exchange material showed significant economic advantages compared to affinity chromatography mode and enabled broader selectivity and enhanced performance compared to anion exchange mode.

The present invention is therefore directed to the chromatographic purification and/or separation of protein glycoforms by contacting the sample, comprising the protein glycoforms, with a separating material, comprising of a hydroxyl group containing base matrix, to the surfaces of which polymer chains are grafted by covalent bonding, characterised in that
   a) the base matrix contains hydroxyl groups,
   b) the polymer chains are covalently bonded to the base matrix via the hydroxyl groups,
   c) the polymer chains comprise end groups —N(Y)—R3 with Y being independently from each other H or $CH_3$, preferably H, and R3 being —CHCOOMR4
   with R4 being C1 to C4 alkyl, like methyl, ethyl, propyl, isopropyl, butyl, isobutyl, preferably isopropyl and isobutyl, very preferred isobutyl, or C1 to C4 perfluoroalkyl
   and M being independently from each other H, Na, K, or $NH_4^+$.

In a preferred embodiment the method of the present invention comprises the steps of
   a) contacting the sample, comprising the protein glycoforms, with a separating material, comprising of a hydroxyl group containing base matrix, to the surfaces of which polymer chains are grafted by covalent bonding, whereby one or more of the protein glycoforms are bound to the separation material
   b) optionally washing the separation material
   c) contacting the separating material with an elution buffer under conditions in which bound protein glycoforms elute from the separation material In a preferred embodiment, in step c), the elution buffer has a pH higher than the loading buffer. The elution buffer may be applied as step or as gradient.

In a preferred embodiment, in step a), the contacting of the sample with the separation material takes place under conditions of increased conductivity, so that the sample loaded onto the separation materials has a conductivity between 5 and 60 mS/cm, preferably between 15 and 35 mS/cm. This is typically achieved by adding salts like sodium chloride to the sample solution.

In another preferred embodiment, the method includes recovering protein glycoforms which flow through the separation material.

In a preferred embodiment, the sample comprises mannose rich protein glycoforms.

In another preferred embodiment, the sample comprises terminal mannose protein glycoforms.

In another preferred embodiment, the sample comprises fucosylated and non-fucosylated protein glycoforms.

In another preferred embodiment, the sample comprises glycosylated and non-glycosylated protein.

In another preferred embodiment, the sample comprises antibodies and/or Fc fusion proteins and/or viral protein glycoforms either isolated or on a virus or virus capsid.

Preferably, the monomer units of the polymers are linked in a linear manner and each monomer unit comprises an end group —N(Y)—R3.

Preferably, the ionic density of the separation material is between 10-1200 µeq/g.

In a preferred embodiment, Y is H and R4 is isopropyl and/or isobutyl.

In a preferred embodiment, the hydroxylgroup containing base matrix comprises aliphatic hydroxyl groups.

In a preferred embodiment, the base matrix is a copolymer formed by copolymerisation of at least one compound from the group a) and b) with
   a) at least one hydrophilically substituted alkyl vinyl ether of the formula I

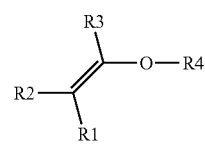

I where R1, R2, R3, independently of one another, can be H or C1 to C6 alkyl, preferably H or —$CH_3$,
and R4 is a radical which carries at least one hydroxyl group
and
   b)
at least one crosslinking agent conforming to formula II and/or III and/or IV with

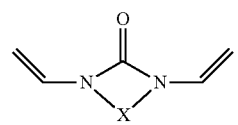

II where X is a divalent alkyl radical having 2 to 5 C atoms, preferably 2 or 3 C atoms, in which one or more methylene groups which are not adjacent and are not located in the direct vicinity of N may be replaced by O, C=O, S, S=O, $SO_2$, NH, NOH or N and one or more H atoms of the methylene groups may be substituted, independently of one another, by hydroxyl groups, C1-C6-alkyl, halogen, $NH_2$, C5-C10-aryl, NH—(C1-C8)-alkyl, N—(C1-C8)-alkyl$_2$, C1-C6-alkoxy or C1-C6-alkyl-OH, and

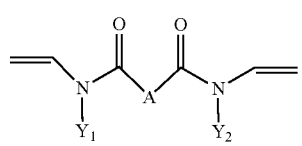

III

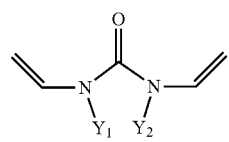

IV where Y1 and Y2 in formula III and IV are, independently of one another,

C1 to C10 alkyl or cycloalkyl, where one or more non-adjacent methylene groups or methylene groups which are not located in the direct vicinity of N may be replaced by O, C=O, S, S=O, $SO_2$, NH, NOH or N and one or more H of the methylene groups may be substituted, independently of one another, by hydroxyl groups, C1-C6-alkyl, halogen, $NH_2$, C5-C10-aryl, NH(C1-C8)alkyl, N(C1-C8)alkyl$_2$, C1-C6-alkoxy or C1-C6-alkyl-OH, or C6 to C18 aryl, where one or more H in the aryl system may be substituted, independently of one another, by hydroxyl groups, C1-C6-alkyl, halogen, $NH_2$, NH(C1-C8)alkyl, N(C1-C8)alkyl$_2$, C1-C6-alkoxy or C1-C6-alkyl-OH and A is a divalent alkyl radical having 2 to 5 C atoms, preferably 2 or 3 C atoms, in which one or more non-adjacent methylene groups or methylene groups which are not located in the direct vicinity of N may be replaced by O, C=O, S, S=O, $SO_2$, NH, NOH or N and one or more H of the methylene groups may be substituted, independently of one another, by hydroxyl groups, C1-C6-alkyl, halogen, $NH_2$, C5-C10-aryl, NH(C1-C8)alkyl, N(C1-C8)alkyl$_2$, C1-C6-alkoxy or C1-C6-alkyl-OH.

R4 in formula I is typically an alkyl radical, a cycloaliphatic radical or an aryl radical which carries at least one hydroxyl group.

In a very preferred embodiment, the base matrix is formed by copolymerisation of a hydrophilically substituted alkyl vinyl ether selected from the group of 1,4-butanediol monovinyl ether, 1,5-pentanediol monovinyl ether, diethylene glycol monovinyl ether or cyclohexanedimethanol monovinyl ether and divinylethyleneurea (1,3-divinylimidazolin-2-one) as crosslinking agent.

In a preferred embodiment, the separation material is preparable by subjecting the hydroxyl group containing base matrix to a cerium (IV) catalysed graft polymerization of monomers according to formula V $$HC=C(R^1)-C(R^2)(=O)-N(R^3)-Y \quad\quad V$$

with $R^1$, $R^2$ and Y being independently from each other H or $CH_3$, preferably H, $R^3$ being —CHCOOM$R^4$ with $R^4$ being C1 to C4 alkyl, like methyl, ethyl, propyl, isopropyl, butyl, isobutyl, preferably isopropyl and isobutyl, very preferred isobutyl, or C1 to C4 perfluoroalkyl and M being H, Na, K, or $NH_4^+$.

This graft polymerization is preferably performed according to U.S. Pat. No. 5,453,186, page 9, Example 8.

In a preferred embodiment, the protein glycoforms are bound to the separation material at a pH between 2 and 7, optionally washed and eluted by increasing the pH value to an alkaline pH, preferably a value above 9, e.g. between 9 and 11, preferably to around 10.

In a preferred embodiment, the sample is applied to the separation material at an ionic density between 10-1200 µeq/g.

In a preferred embodiment, between 10 mg and 100 mg of the glycoproteins are bound per ml of the separation material.

Figure 11:
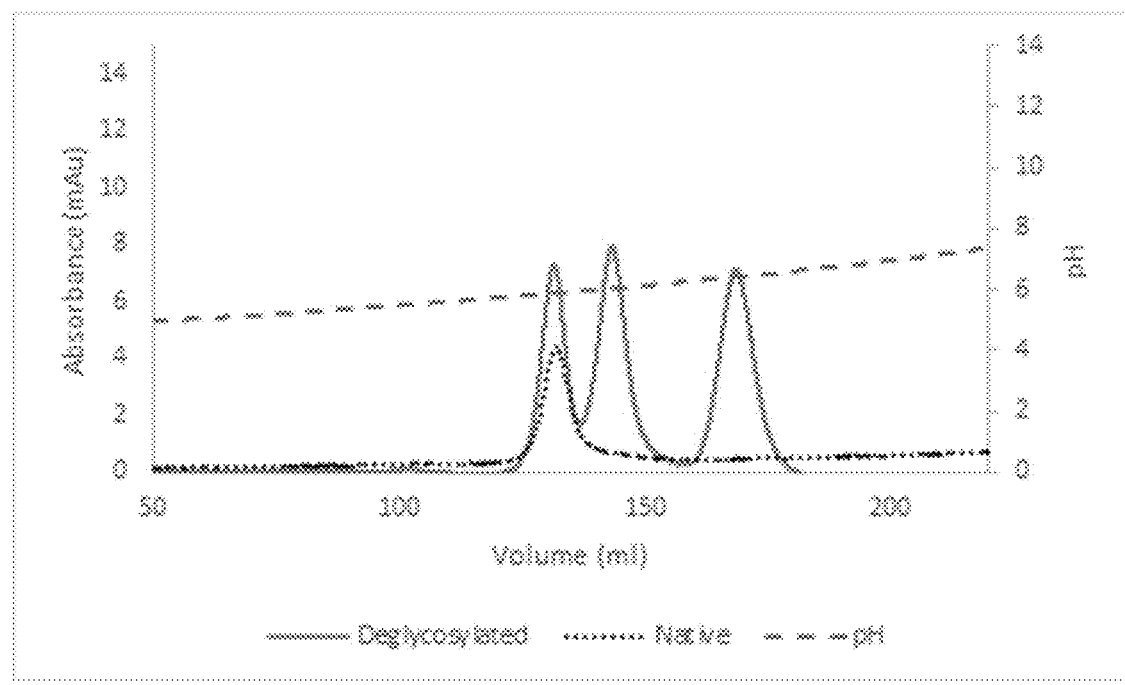

FIG. 11 shows the elution peak of the bound glycoprotein (e.g. Rituximab®) on the separation material at 1 mg/ml CV loading and 150 mM NaCl. UV adsorption signal of the partly degycosylated Rituximab® trace in solid line, the UV adsorption signal of the native Rituximab® in dotted line and pH in dashed line.

Figure 12:
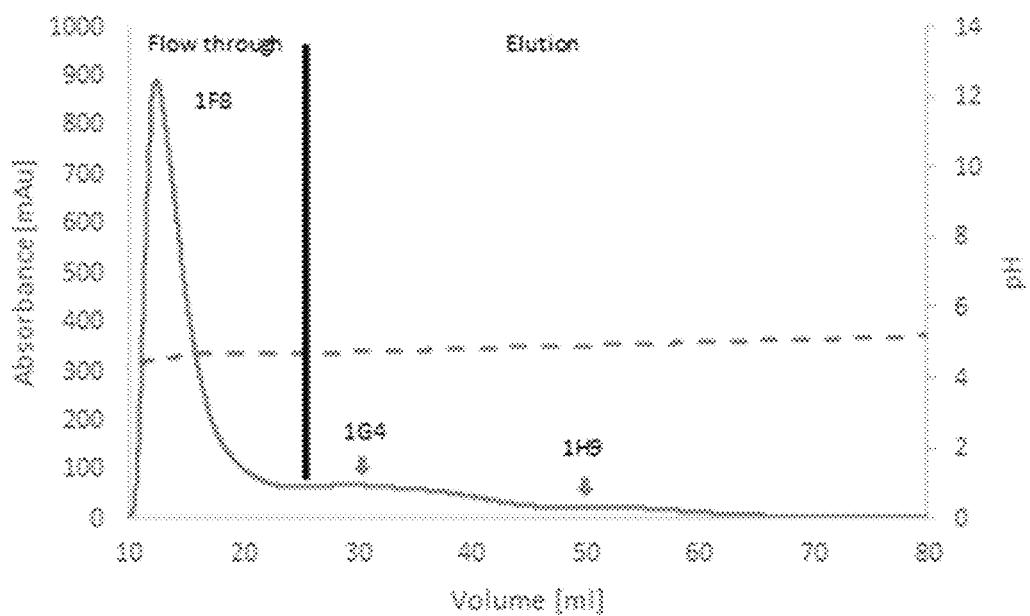

FIG. 12 shows the flow through and elution peak of the bound glycoprotein (e.g. mAb05) on the separation material at 10 mg/ml CV loading and 450 mM NaCl. UV adsorption signal trace in solid line and pH in dashed line.

Figure 13:
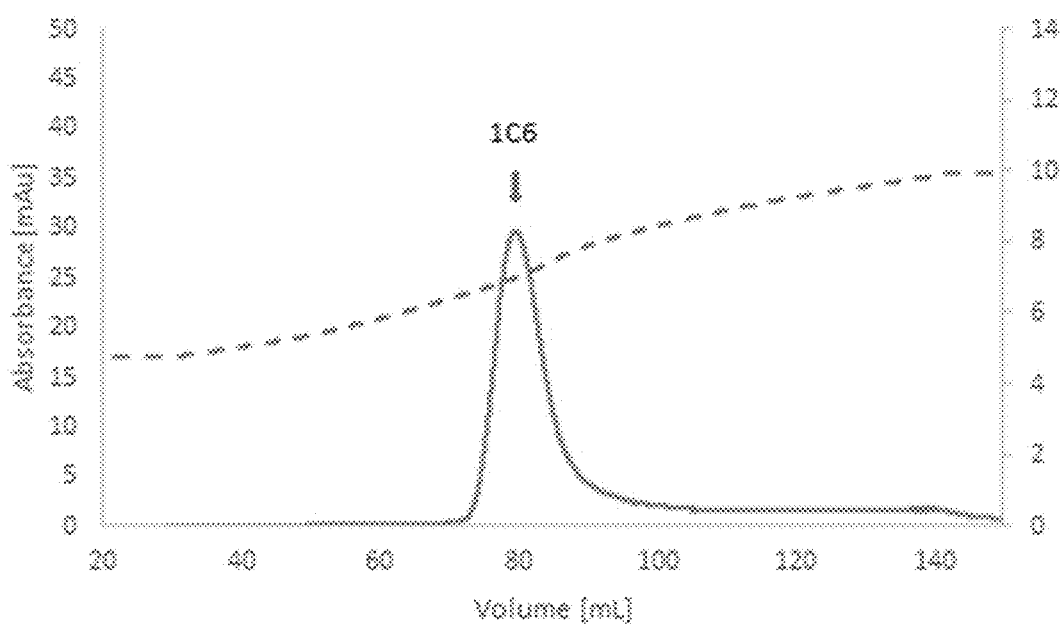

FIG. 13 shows the elution peak of the bound glycoprotein (e.g. Spike S1 protein of SARS-CoV-2) on the separation material at 1 mg/ml CV loading and 150 mM NaCl. UV adsorption signal of the glycoprotein trace in solid line, the and pH in dashed line.

Figure 14:
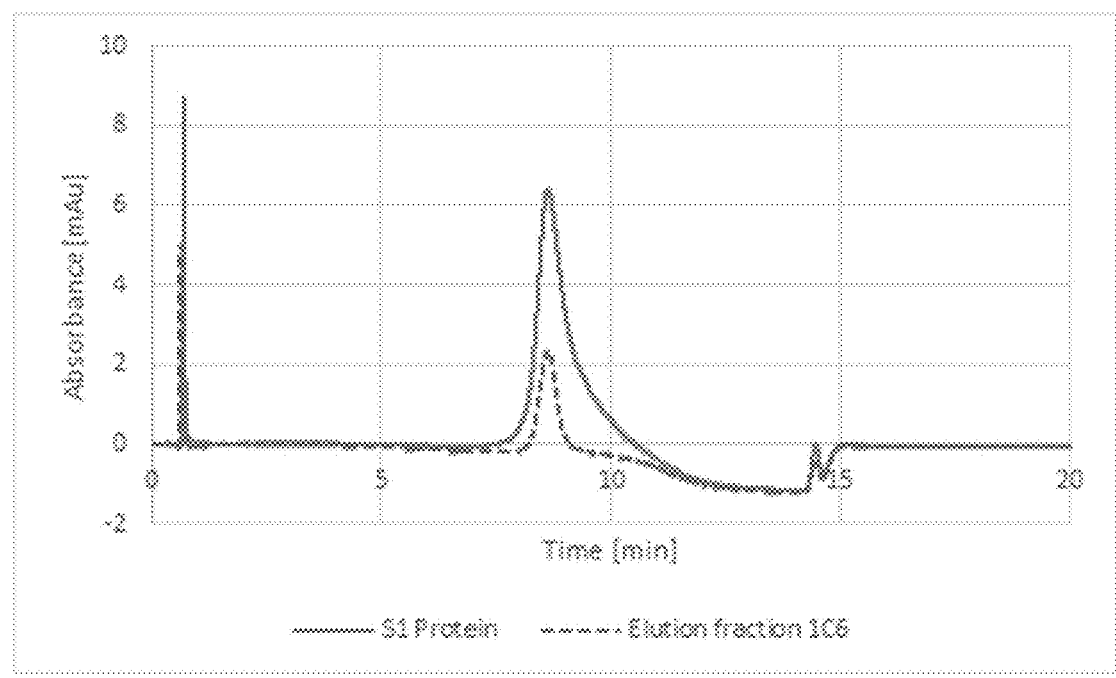

FIG. 14 shows analytical results of the sample fraction characterization using a HIC analytical method displayed in UV signal traces, including loaded glycoprotein (load) at 1 mg glycoprotein/ml CV loading and 250 mM NaCl in solid line and the elution fraction 106 of the glycoprotein (e.g. Spike S1 protein of SARS-CoV-2 in dashed line.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a ligand" includes a plurality of ligands and reference to "an antibody" includes a plurality of antibodies and the like.

Unless defined otherwise, all technical and scientific terms used herein have the same meaning as commonly understood by one of ordinary skill in the art to which this invention is related. The following terms are defined for purposes of the invention as described herein.

As used herein the term "target molecule" refers to any molecule, substance or compound that shall be isolated, separated or purified from one or more other components, e.g. impurities, in a sample. Examples of target molecules are glycoproteins, also called protein glycoforms or glycan species of glycoproteins. Target molecules can also be non-glycosylated proteins which shall be separated from protein glycoforms, which are also present in the sample. In the production and/or purification process the target molecule is typically present in a liquid. The liquid might be water, a buffer, a non-aqueous solvent like ethanol or any mixture thereof. Beside the target molecule said liquid may comprise one or more impurities. The liquid may also be called sample. The composition of the liquid may change during production and/or purification depending on the process steps that are performed. After a chromatographic step the liquid typically comprises other solvents than before, due to the eluent used in the chromatographic step. Typically, only after the very last purification step the target molecule might be dried for preparing the final dosage form.

Glycoproteins or protein glycoforms are proteins which are glycosylated. Glycosylation can for example be in the form of mono-di- or oligosaccharide chains, comprising of one or more fucose, mannose, galactose, N-acetylglucosamine, sialic acid and/or neuraminic acid. For example, antibodies typically have complex N-linked oligosaccharides. Further information can be found above in the introduction. An example for a common glycan structure is N-glycoside-linked sugar chains, as can be found in antibodies.

A "N-glycoside-linked sugar chain" or "N-glycoside-linked glycan" is typically bound to asparagine 297 (according to the number of Kabat), although a complex N-glycoside linked sugar chain can also be linked to other asparagine residues. The complex N-glycoside-linked sugar chain typically has a biantennary composite sugar chain, mainly having the following structure:

N-acetylglucosamine ("GlcNAc") of the reducing terminal, typically by an α 1,6 bond (the 6-position of GlcNAc is linked to the 1-position of fucose). "Gal" refers to galactose, and "Man" refers to mannose.

Examples of protein glycoforms are proteins with differing levels of fucosylation, e.g. differing levels of core fucosylation, differing levels of sialylation, differing levels of galactosylation or differing levels of mannosylation. Preferably, the method of the present invention is used to separate or purify high mannose protein glycoforms.

High mannose protein glycoforms are glycoproteins having a glycan residue with five or more, typically five to nine, mannose units. An example for high mannose proteins are antibodies having an N-linked oligosaccharide comprising 5 to 9 mannose units. Another example for mannose rich proteins are viral glycoproteins like the mannose rich envelope glycoproteins of HIV 1 or the spike (S1) protein of 2019-nCoV (SARS-CoV-2).

Terminal mannose protein glycoforms are glycoproteins having a glycan residue with 3 mannose units in the core structure, where one or both mannose units in the branches are not bound to N-acetylglucosamine ("GlcNAc"). In some embodiments this may refer to G0-N glycoproteins. In some embodiments this may refer to G1-N glycoproteins. In some embodiments this may refer to hydrid glycoforms.

Glycoproteins or protein glycoforms according to the present invention can be an isolated glycoprotein or glycoproteins linked to other moieties like drugs, other proteins, viruses or virus capsids. In some embodiments, the protein glycoforms are produced in mammalian cells, in fungal cells, in insect cells or in plant cells.

The term "antibody" refers to a protein which has the ability to specifically bind to an antigen. "Antibody" or "IgG" further refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes IgG, IgM, IgA, IgD, and IgE, respectively.

An exemplary immunoglobulin (antibody) structural unit is composed of two pairs of polypeptide chains, each pair having one "light" (about 25 kD) and one "heavy" chain

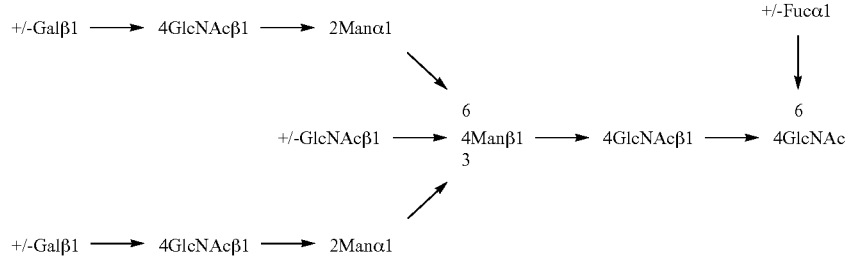

where +/− indicates that the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to (about 50-70 kD), said chains being stabilized, for example, by interchain disulfide bonds. The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies may be monoclonal or polyclonal and may exist in monomeric or polymeric form, for example, IgM antibodies which exist in pentameric form and/or IgA antibodies which exist in monomeric, dimeric or multimeric form. Antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins. According to the present invention fusion proteins are also encompassed by the term "antibody".

In some embodiments, an antibody is an Fc region containing protein, e.g., an immunoglobulin. In some embodiments, an Fc region containing protein is a recombinant protein which includes the Fc region of an immunoglobulin fused to another polypeptide or a fragment thereof. Exemplary polypeptides include, e.g., renin; a growth hormone, including human growth hormone and bovine growth hormone; growth hormone releasing factor; parathyroid hormone; thyroid stimulating hormone; lipoproteins; α-1-antitrypsin; insulin α-chain; insulin β-chain; proinsulin; follicle stimulating hormone; calcitonin; luteinizing hormone; glucagon; clotting factors such as factor VIIIC, factor IX, tissue factor, and von Willebrand factor; anti-clotting factors such as Protein C; atrial natriuretic factor; lung surfactant; a plasminogen activator, such as urokinase or tissue-type plasminogen activator (t-PA); bombesin; thrombin; hemopoietic growth factor; tumor necrosis factor-α and -β; enkephalinase; RANTES (regulated on activation normally T-cell expressed and secreted); human macrophage inflammatory protein (MIP-1-α); a serum albumin such as human serum albumin; Muellerian-inhibiting substance; relaxin α-chain; relaxin β-chain; prorelaxin; mouse gonadotropin-associated peptide; a microbial protein, such as β-lactamase; DNase; IgE; a cytotoxic T-lymphocyte associated antigen (CTLA) (e.g., CTLA-4); inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as αFGF and βFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(I-3)-IGF-I (brain IGF-I), insulin-like growth factor binding proteins (IGFBPs); CD proteins such as CD3, CD4, CD8, CD 19 CD20, CD34, and CD40; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-I to IL-IO; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CDI Ia, CDI Ib, CDI Ic, CD 18, an ICAM, VLA-4 and VCAM; a tumor associated antigen such as HER2, HER3 or HER4 receptor; and fragments and/or variants of any of the above-listed polypeptides. In addition, an antibody according to the present invention is any protein or polypeptide, fragment or variant thereof, that binds specifically to any of the above-listed polypeptides.

As used herein, and unless stated otherwise, the term "sample" refers to any composition or mixture that contains a target molecule. Samples may be derived from biological or other sources. Biological sources include eukaryotic sources like animals or humans. Preferred samples are blood or plasma samples derived from mammalians. The sample may also include diluents, buffers, detergents, and contaminating species and the like that are found mixed with the target molecule. The sample may be "partially purified" (i.e., having been subjected to one or more purification steps, such as filtration or centrifugation steps) or may be obtained directly from an organism producing the target molecule. A plasma sample is any sample comprising plasma or parts of plasma.

The term "impurity" or "contaminant" as used herein, refers to any foreign or objectionable molecule, including a biological macromolecule such as DNA, RNA, one or more host cell proteins, nucleic acids, endotoxins, lipids, impurities of synthetic origin and one or more additives which may be present in a sample containing the target molecule that is being separated from one or more of the foreign or objectionable molecules. The term "impurity" or "contaminant" as used herein can also be applied to certain immunoglobulins which need to be separated from the target molecule like immunoglobulin A which causes allergic reactions in patients as well as immunoglobulin M. Additionally, such impurity may include any reagent which is used in a step of the production and/or purification process.

The terms "purifying", "separating", or "isolating", as used interchangeably herein, refer to increasing the degree of purity of a target molecule by separating it from a composition or sample comprising the target molecule and one or more other components, e.g. impurities. Typically, the degree of purity of the target molecule is increased by removing (completely or partially) at least one impurity from the composition.

The term "chromatography" refers to any kind of technique which separates an analyte of interest (e.g. a target molecule) from other molecules present in a mixture. Usually, the target molecule is separated from other molecules as a result of differences in rates at which the individual molecules of the mixture migrate through a stationary medium or separation material under the influence of a moving phase, or in bind and elute processes. Examples for chromatographic separation processes are reversed phase chromatography, ion exchange chromatography, size exclusion chromatography, affinity chromatography, hydrophobic interaction chromatography and mixed mode chromatography.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, glycine and ammonium buffers, as well as combinations of these.

The term "separation material" or "chromatography matrix" are used interchangeably herein and refer to any kind of particulate sorbent, resin, matrix or solid phase which in a separation process separates a target molecule (e.g., an Fc region containing protein such as an immunoglobulin) from other molecules present in a mixture. Usually, the target molecule is separated from other molecules as a result of differences in rates at which the individual molecules of the mixture migrate through the separation material and interact with the separation material under the influence of a moving phase, or in bind and elute processes. The separation material consisting of e.g. resin particles, membranes or monolithic sorbents can be put in columns or cartridges. Typically, the separation material comprises a base matrix as base material and one or more types of ligands attached to said base matrix.

A "ligand" is or comprises a functional group and is attached to the chromatography base matrix and determines or influences the binding properties of the matrix. Preferably, the ligands are polymer chains carrying one or more, preferably a plurality of functional groups. Most preferred are ligands made of polymer chains which carry at least one functional group per monomer unit from which they are built. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Preferred ligands that can be used herein include, but are not limited to, are weak ion exchange groups, such as carboxylic acid.

The term "ion-exchange" and "ion-exchange chromatography" refers to the chromatographic process in which a target molecule (e.g., an Fc region containing target protein) in a mixture interacts with a charged compound linked (such as by covalent attachment) to an ion exchange matrix such that the target molecule interacts non-specifically with the charged compound more or less than solute impurities or contaminants in the mixture. The impurities in the mixture elute from a column of the ion exchange material faster or slower than the target molecule or are bound to or excluded from the resin relative to the target molecule. "Ion-exchange chromatography" specifically includes cation exchange, anion exchange, and mixed mode ion exchange chromatography. Ion exchange chromatography can bind the target molecule (e.g., an Fc region containing target protein) followed by elution or can predominately bind the impurities while the target molecule "flows through" the column. Preferably, the ion exchange chromatography step is performed in a bind and elute mode.

The phrase "ion exchange matrix" refers to a chromatography medium or separation material which is negatively charged (i.e. a cation exchange resin) or positively charged (i.e. an anion exchange resin). The charge may be provided by attaching one or more charged ligands to the matrix, e.g. by covalent linking. Alternatively, or in addition, the charge may be an inherent property of the matrix.

The term "cation exchange matrix" is used herein to refer to a separation material which is negatively charged, e.g. having one or more negatively charged ligands, such as carboxylic acid groups, attached thereto. When "loading" a separation column in bind and elute mode, a buffer is used to load the sample or composition comprising the target molecule (e.g., an Fc region containing target protein) and one or more impurities onto a chromatography column (e.g., an ion exchange column). The buffer has a conductivity and/or pH such that the target molecule is bound to the separation material while ideally all the impurities are not bound and flow through the column.

When "loading" a separation column to "flow through" a target molecule, a buffer is used to load the sample or composition comprising the target molecule (e.g., an Fc region containing target protein) and one or more impurities onto a chromatography column (e.g., an ion exchange column). The buffer has a conductivity and/or pH such that the target molecule is not bound to the separation material and flows through the column while ideally all the impurities are bound the column.

When "loading" a separation column to "bind and elute" a target molecule, a buffer is used to load the sample or composition comprising the target molecule (e.g., an Fc region containing target protein) and one or more impurities onto a chromatography column (e.g. an ion exchange column). The buffer has a conductivity and/or pH such that the target molecule is bound to the separation material. The separation from the one or more impurities follows with a change of conductivity and/or pH such that the target molecule is washed or eluted before or after one or more impurities. Typically, the buffer in which the sample is loaded on the separation material is called loading buffer or sample buffer.

The term "equilibrating" refers to the use of a buffer to equilibrate the separation material prior to loading the target molecule. Typically, the loading buffer is used for equilibrating.

By "wash" or "washing" a separation material is meant passing an appropriate liquid, e.g. a buffer through or over the separation material. Typically washing is used to remove weakly bound contaminants from the separation material prior to eluting the target molecule and/or to remove non-bound or weakly bound target molecule after loading.

In this case, typically, the wash buffer and the loading buffer are the same. If virus inactivation buffer is used, it is used to inactivate certain present viruses prior to eluting the target molecule. In this case, typically, the virus inactivation buffer differs from loading buffer since it may contain detergent/detergents or have different properties (pH/conductivity/salts and their amounts).

Washing can also be used to remove contaminants from the separation material after the elution of the target molecule. This is done by passing an appropriate liquid, e.g. a buffer through or over the separation material after the elution of the target molecule. In this case, typically, the washing buffer differs from the loading buffer. It may contain detergent/detergents or have different properties (pH/conductivity/salts and their amounts). The washing buffer is for example an acidic buffer.

To "elute" a molecule (e.g., a polypeptide of interest like Immunoglobulin G or an impurity) from a separation material is meant to remove the molecule therefrom. Elution may take place directly in flow though mode when the target molecule is eluted with the solvent front of the loading buffer. Or by altering the solution conditions such that a buffer different from the loading buffer competes with the molecule of interest for the ligand sites on the separation material. A non-limiting example is to elute a molecule from an ion exchange material by altering the ionic strength of the buffer surrounding the ion exchange material, such that the buffer competes with the molecule for the charged sites on the ion exchange material.

The term "average particle size diameter" or d50 means the average particle size distribution value at 50% of the cumulative particle size distribution. Particle size is determined by laser-diffraction, preferably with Malvern 'Master Sizer.

The term "average pore size" means the average pore size distribution value at 50% of the cumulative pore size distribution.

The terms "flow-through process", "flow-through mode", and "flow-through operation", as used interchangeably herein, refer to a separation technique in which at least one target molecule (e.g., an Fc-region containing protein or an antibody) contained in a sample along with one or more impurities is intended to flow through a separation material, which usually binds one or more impurities, where the target molecule usually does not bind (i.e., flows through) and is eluted from the separation material with the loading buffer. The terms "bind and elute mode" and "bind and elute process", as used herein, refer to a separation technique in which at least one target molecule contained in a sample (e.g., an Fc region containing protein) binds to a suitable separation material (e.g., an ion exchange chromatography media) and is subsequently eluted with a buffer different from the loading buffer.

The term "ionic density" as used herein, refers to number of ions per unit of volume or mass of a given separation material, more particularly, the number of ions of given type (e.g. positive ions or negative ions) per unit volume or mass of separation material. Usually the number of ions is estimated titrating the given separation material. Moreover, the amount of the ions is given in equivalents (eq) per mass or volume unit for separation material.

The term "conductivity" as used herein, refers to an inherent property of most materials, that quantifies how strongly it resists or conducts electric current. In aqueous solutions, such as buffers, the electrical current is carried by charged ions. The conductivity is determined by the number of charged ions, the amount of charge they carry and how fast they move. Hence, for most aqueous solutions, the higher the concentration of dissolved salts, the higher the conductivity. Raising the temperature enables the ions to move faster, hence increasing the conductivity. Typically, the conductivity is defined in room temperature, if not otherwise indicated. The basic unit of conductance is Siemens (S). It is defined as the reciprocal of the resistance in Ohms, measured between the opposing faces of a 1 cm cube of liquid. Therefore, the values are estimated in S/cm.

The present invention provides methods of separating or purifying protein glycoforms. This means that one or more protein glycoforms can be separated from one or more other protein glycoforms and/or from other impurities in a sample. Preferably at least one protein glycoform is separated from at least one other glycoform, e.g. one high mannose glycoform is separated from another protein glycoform. This is done by a chromatographic separation on certain separation materials, also called resins, comprising a base matrix to which polymer chains are covalently attached. The polymer chains are made of monomers which comprise an amino acid and a polymerizable double bond.

By the methods of the invention glycoforms can be separated, enriched and/or purified enabling an efficient glycan specie separation. In particular aspects of the invention, it is beneficial to separate glycan variants containing high mannose or terminal mannose molecules which are more hydrophobic and demonstrate faster clearance. Moreover, such glycan variants may contribute to higher toxicity and lower glycoprotein efficacy. In other aspects of the invention, it is beneficial to separate glycoproteins bearing fucose, assuring the better control of antibody-dependent cell-mediated cytotoxity (ADCC) activity. In other aspects of the invention, it is beneficial to eliminate proteins which are otherwise identical to the target glycoproteins, but which are not glycosylated. In one embodiment of the invention the purified glycoprotein contains no high mannose glycan variants. In another embodiment of the invention the purified glycoprotein contains low level of hybrid glycan variants with terminal mannose. In another embodiment of the invention the purified glycoprotein contains low level of non-fucosylated glycan variants. In another embodiment of the invention the purified glycoprotein contains low level of non-glycosylated protein.

The separation materials of the present invention comprise a base material to which tentacle-like structures are attached, preferably grafted.

The base material, also called base matrix, contains reactive groups which are accessible to the graft-polymerisation reaction, in particular OH groups, preferably aliphatic OH groups. Base materials can therefore also be prepared, for example, from organic polymers. Organic polymers of this type can be polysaccharides, such as agarose, dextrans, starch, cellulose, etc., or synthetic polymers, such as poly(acrylamides), poly(methacrylamides), poly(acrylates), poly(methacrylates), hydrophilically substituted poly(alkyl allyl ethers), hydrophilically substituted poly(alkyl vinyl ethers), poly(vinyl alcohols), poly(styrenes) and copolymers of the corresponding monomers. These organic polymers can preferably also be employed in the form of a crosslinked hydrophilic network. This also includes polymers made from styrene and divinylbenzene, which can preferably be employed, like other hydrophobic polymers, in a hydrophilized form.

Alternatively, inorganic materials, such as silica, zirconium oxide, titanium dioxide, aluminium oxide, etc., can be employed as base materials. It is equally possible to employ composite materials, i.e., for example, particles which can themselves be magnetised by copolymerisation of magnetisable particles or of a magnetisable core. It is also possible to use core shell materials whereby the shell, i.e. at least the surface or a coating, has OH groups.

However, preference is given to the use of hydrophilic base materials which are stable to hydrolysis or can only be hydrolysed with difficulty since the materials according to the invention should preferably withstand alkaline cleaning or regeneration at e.g. basic pH over an extended use duration.

The base matrix may consist of irregularly shaped or spherical particles, whose particle size can be between 2 and 1000 μm. Preference is given to average particle sizes between 3 and 300 μm, in a most preferred embodiment the average particle size is between 20-63 μm.

The base matrix may, in particular, be in the form of non-porous or preferably porous particles. The average pore sizes can be between 2 and 300 nm. Preference is given to pore sizes between 5 and 200 nm, most preferred average pore size is between 40-110 nm.

The base matrix may equally also be in the form of membranes, fibres, hollow fibres, coatings or monolithic mouldings. Monolithic mouldings are, preferably porous, three-dimensional bodies, for example in cylindrical form.

In a preferred embodiment, the base matrix is a copolymer formed by copolymerisation of at least one compound from the group a) and b) with a) at least one hydrophilically substituted alkyl vinyl ether of the formula I

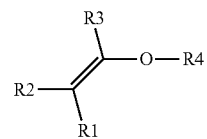

I where R1, R2, R3, independently of one another, can be H or C1 to C6 alkyl, preferably H or —CH₃,
and R4 is a radical which carries at least one hydroxyl group and
b)
at least one crosslinking agent conforming to formula II and/or III and/or IV with

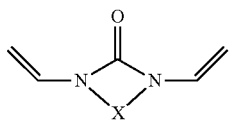

where X is a divalent alkyl radical having 2 to 5 C atoms, preferably 2 or 3 C atoms, in which one or more methylene groups which are not adjacent and are not located in the direct vicinity of N may be replaced by O, C=O, S, S=O, SO₂, NH, NOH or N and one or more H atoms of the methylene groups may be substituted, independently of one another, by hydroxyl groups, C1-C6-alkyl, halogen, NH₂, C5-C10-aryl, NH-(C1-C8)-alkyl, N-(C1-C8)-alkyl₂, C1-C6-alkoxy or C1-C6-alkyl-OH, and

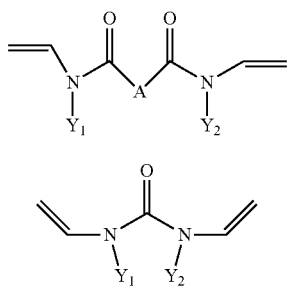

where Y1 and Y2 in formula III and IV are, independently of one another,
C1 to C10 alkyl or cycloalkyl, where one or more non-adjacent methylene groups or methylene groups which are not located in the direct vicinity of N may be replaced by O, C=O, S, S=O, SO₂, NH, NOH or N and one or more H of the methylene groups may be substituted, independently of one another, by hydroxyl groups, C1-C6-alkyl, halogen, NH₂, C5-C10-aryl, NH(C1-C8)alkyl, N(C1-C8)alkyl₂, C1-C6-alkoxy or C1-C6-alkyl-OH, or C6 to C18 aryl, where one or more H in the aryl system may be substituted, independently of one another, by hydroxyl groups, C1-C6-alkyl, halogen, NH₂, NH(C1-C8)alkyl, N(C1-C8)alkyl₂, C1-C6-alkoxy or C1-C6-alkyl-OH and
A is a divalent alkyl radical having 2 to 5 C atoms, preferably 2 or 3 C atoms, in which one or more non-adjacent methylene groups or methylene groups which are not located in the direct vicinity of N may be replaced by O, C=O, S, S=O, SO₂, NH, NOH or N and one or more H of the methylene groups may be substituted, independently of one another, by hydroxyl groups, C1-C6-alkyl, halogen, NH₂, C5-C10-aryl, NH(C1-C8)alkyl, N(C1-C8)alkyl₂, C1-C6-alkoxy or C1-C6-alkyl-OH.
R4 in formula I is typically an alkyl radical, a cycloaliphatic radical or an aryl radical which carries at least one hydroxyl group.

In a very preferred embodiment, the base matrix is formed by copolymerisation of a hydrophilically substituted alkyl vinyl ether employed selected from the group of 1,4-butanediol monovinyl ether, 1,5-pentanediol monovinyl ether, diethylene glycol monovinyl ether or cyclohexane-dimethanol monovinyl ether and divinylethyleneurea (1,3-divinylimidazolin-2-one) as crosslinking agent.
An example of a suitable commercially available vinylether based base material is Eshmuno®, Merck KGaA, Germany.
To the surfaces of the base material linear polymer chains are covalently bonded so that a separation material is generated whereby
a) the base material contains preferably aliphatic hydroxyl groups,
b) the polymers are covalently bonded to the support,
c) the polymers comprise amino acid residues,
d) the monomer units of the polymers are linked in a linear manner.
The actual separation material comprising the base material and the covalently attached linear polymer chains can be prepared in various ways. In the case of "grafting onto", polymer chains must firstly be formed from the monomers and bound to the surface in a second step. In the case of "grafting from", a polymerisation reaction is initiated on the surface, and the graft polymer is built up directly from individual monomers. Other polymerisation methods which allow binding to the surface of the base material can also be employed.
Preference is given to the "grafting from" method and particular preference is given to variants in which only a few by-products are formed, such as a non-covalently bonded polymer, which have to be separated off. Processes with controlled free-radical polymerisation, such as, for example, the method of atom-transfer free-radical polymerisation (ATRP), appear particularly interesting. Here, an initiator group is covalently bonded to the support surface in the desired density in a first step. An initiator group can be, for example, a halide bonded via an ester function, as in a 2-bromo-2-methylpropionic acid ester. The graft polymerisation is carried out in a second step in the presence of copper(I) salts.
A very preferred one-step graft polymerisation reaction suitable for the production of the separation materials to be used in the present invention can be initiated by cerium(IV) on a hydroxyl-containing base material, without the base material having to be activated.
This cerium(IV) initiated grafting is preferably carried out in accordance with EP 0 337 144 or U.S. Pat. No. 5,453,186. The chain produced is linked to the base material via a monomer unit. To this end, the base material according to the invention is suspended in a solution of monomers, preferably in an aqueous solution. The grafting-on of the polymeric material is effected in the course of a conventional redox polymerisation with exclusion of oxygen. The polymerisation catalyst employed is cerium(IV) ions, since this catalyst forms free-radical sites on the surface of the base material, from which the graft polymerisation of the monomers is initiated. This reaction is normally carried out in dilute mineral acids. In order to carry out this graft polymerisation, the acid is usually employed in an aqueous solution with a concentration in the range from 1 to 0.00001 mol/l, preferably from 0.1 to 0.001 mol/l. Very particular preference is given to the use of dilute nitric acid, which is employed with a concentration in the range from 0.1 to 0.001 mol/l.
For the preparation of the separating materials according to the invention, the monomers are normally added in excess to the base material. Typically, 0.05 to 100 mol of total monomer are employed per litre of sedimented polymer material, preferably 0.05-25 mol/l are employed.

The polymerisation is terminated by termination reactions involving the cerium salts. For this reason, the (average) chain length can be influenced by the concentration ratios of the base material, the initiator and the monomers. Furthermore, uniform monomers or also mixtures of different monomers can be employed; in the latter case, grafted copolymers are formed.

The monomers to be favourably used for the preparation of the separation materials to be used in the present invention are those according to formula V

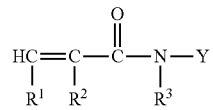

V with $R^1$, $R^2$ and Y being independently from each other H or $CH_3$, preferably H.
$R^3$ being —CHCOOMR$^4$

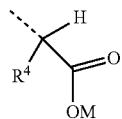

with $R^4$ being C1 to C4 alkyl, like methyl, ethyl, propyl, isopropyl, butyl, isobutyl, preferably isopropyl and isobutyl, very preferred isobutyl, or C1 to C4 perfluoroalkyl
and M being H, Na, K, or $NH_4^+$.

Perfluoroalkyl means that all H atoms of the alkyl residue are substituted by F atoms.

Exemplary, preferred structures of formula V are Va

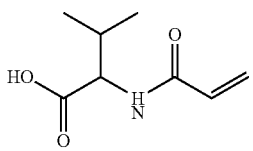

Va with $R^1$, $R^2$ and Y being H
$R^3$ being —CHCOOMR$^4$
with $R^4$ being isopropyl
and M being H
as well as Formula Vb

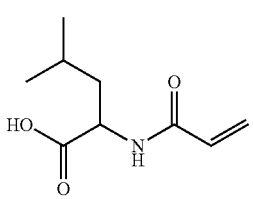

Vb with $R^1$, $R^2$ and Y being H
$R^3$ being —CHCOOMR$^4$
with $R^4$ being isobutyl
and M being H Such monomers can also be described as acryloylvalin (formula Va), acryloylleucine (formula Vb), acryloylalanine, acryloylnorleucine, methacryloylvalin, methacryloylleucine, methacryloylalanine, methacryloylnorleucine, dimethacryloylvalin, dimethacryloylleucine, dimethacryloylalanine, dimethacryloylnorleucine, whereby acryloylvalin and acryloylleucine are preferred, acryloylleucine is especially preferred.

The separation materials to be used in the method of the present invention preferably only contain tentacle-like linear polymer structures grafted onto the base material that are built from monomers according to formula V. Preferably, they contain linear polymers that are only build by one type of monomer according to formula V.

But it is also possible that the linear polymers are built by co-polymerization of two or more different monomers according to formula V. It is also possible that the linear polymers are built by co-polymerization of one or more different monomers according to formula V and one or more other polymerizable monomers like other acrylamides, methacrylates, acrylates, methacrylates etc. which are functionalized e.g. with ionic, hydrophilic or hydrophobic groups.

Figure 1:
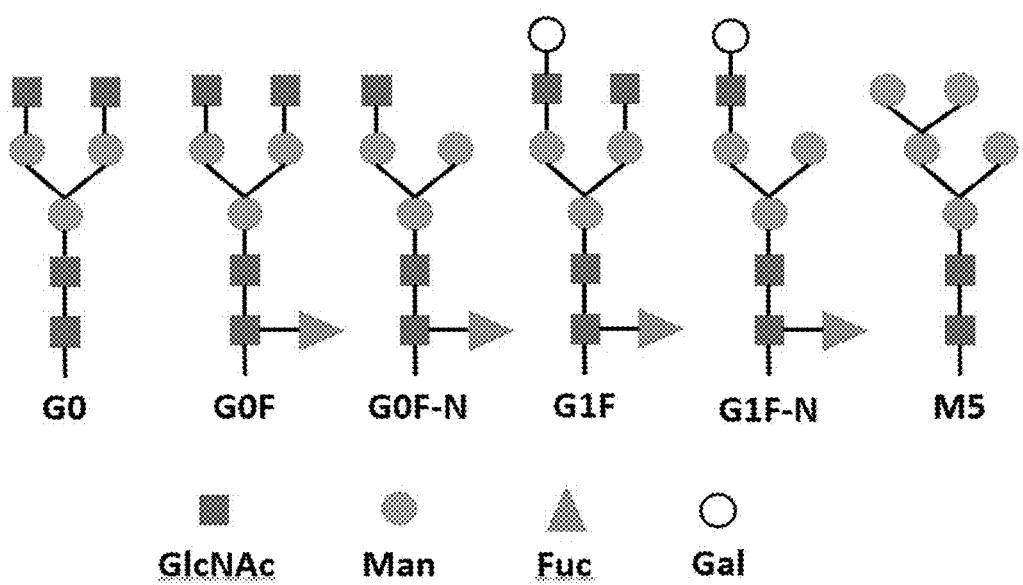
FIG. 1 shows a schematic view of glycan structures, where squares represent N-acetylglucosamine (GlcNAc), full circles—mannose, triangles—fucose (Fuc) and empty circles—galactose (Gal).
Figure 2:
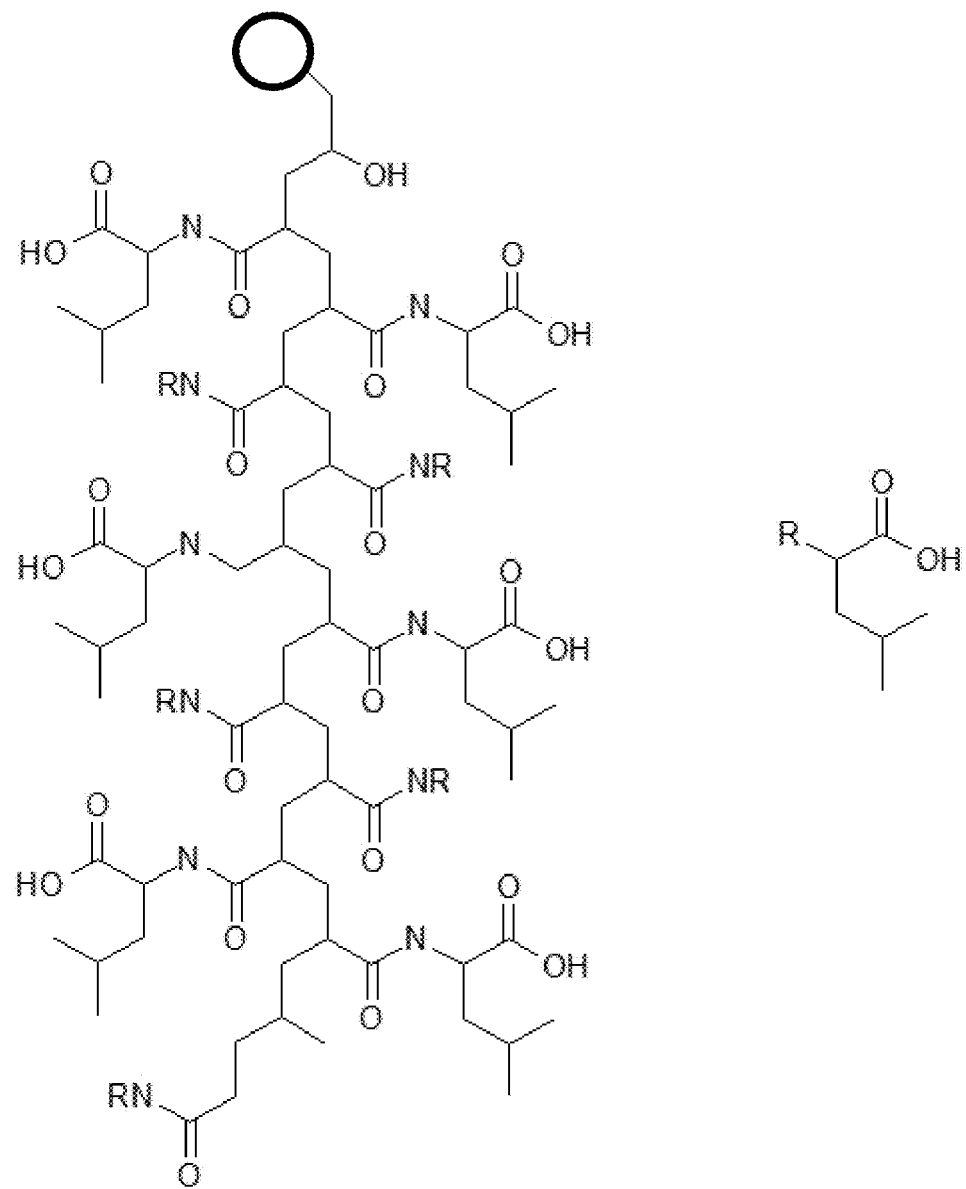
FIG. 2 shows a schematic view of a separation material according to the present invention with the base material (dot) that is functionalized with a linear polymer built by polymerization of acryloylleucine monomers.
Figure 3:
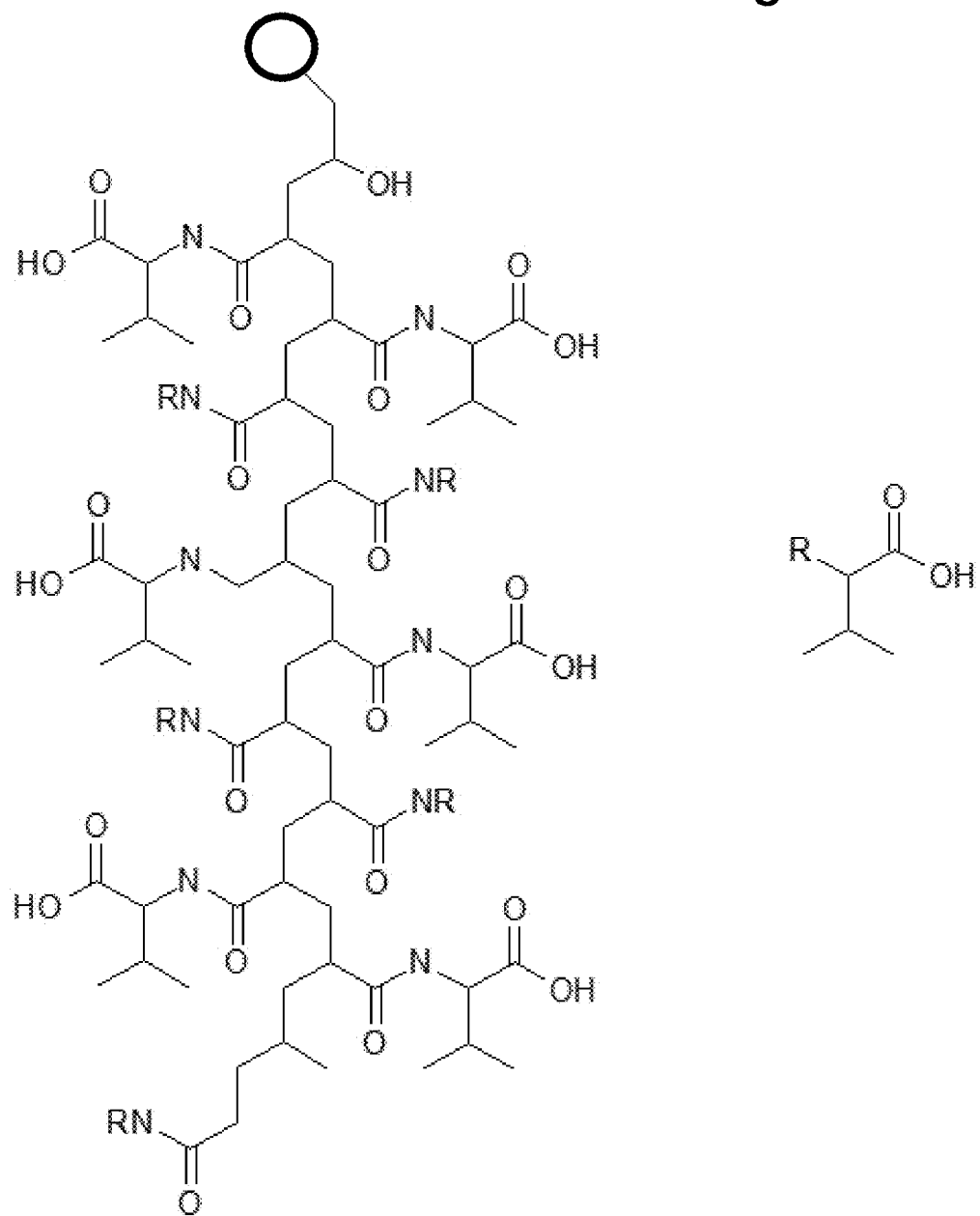
FIG. 3 shows a schematic view of a separation material according to the present invention with the base material (dot) that is functionalized with a linear polymer built by polymerization of acryloylvaline monomers.

Exemplary structures of the separation materials according to the present invention are shown in FIGS. 2 and 3. FIG. 2 shows the base material (dot) that is functionalized with a linear polymer built by polymerization of acryloylleucine monomers. Additionally, for clarification, the carboxy-alkyl endgroup of each polymer unit is shown. FIG. 3 shows the base material (dot) that is functionalized with a linear polymer built by polymerization of acryloylvaline monomers. Additionally, for clarification, the carboxy-alkyl endgroup of each polymer unit is shown.

In a preferred embodiment, the separation material to be used in the method of the present invention is an ion exchange material with varying amount of ionic density window ranging from 10-1200 μeq/g, where in more preferred embodiment the ionic density window is between 400-900 μeq/g.

In a preferred embodiment, the ion exchange material can contain ion exchange functional groups and hydrophobic functional groups, where in more preferred embodiment both functional groups are on a single surface functional unit resulting from the one monomeric unit that has been built into the polymeric chain, where in the most preferred embodiment the functional groups are part of an amino acid residue.

Typically, a chromatography column comprising the above described separation materials is used in the method according to the present invention. Chromatography columns are known to a person skilled in the art. They typically comprise cylindrical tubes or cartridges filled with the separation material as well as filters and/or means for fixing the separation material in the tube or cartridge and connections for solvent delivery to and from the tube. The size of the chromatography column varies depending on the application, e.g. analytical or preparative. A chromatography column can also be a membrane containing cartridge.

The materials to be used in the method of the invention can also be described as base materials provided with separation effectors. They can be used for the selective, partially selective or non-selective binding or adsorption of one or more target components with the aim of separation out of a sample liquid, or for the selective, partially selective or non-selective binding or adsorption of one or more secondary components with the aim of separation of the secondary component out of a matrix, the isolation, enrichment and/or depletion of biopolymers from natural sources, the isolation, enrichment and/or depletion of biopolymers from recombinant sources, the isolation, enrichment and/or depletion of proteins and peptides, the isolation, enrichment and/or depletion of monoclonal and polyclonal antibodies, the isolation, enrichment and/or depletion of viruses, the isolation, enrichment and/or depletion of host cell proteins, or the isolation, enrichment and/or depletion of glycoproteins. Preferred target molecules are glycoproteins.

The target molecules are separated from at least one or more other substances from a sample, where the sample which comprises the target molecule is dissolved in a liquid, which is brought into contact with the material according to the invention. Contact times are usually in the range from 30 seconds to 24 hours. It is advantageous to work in accordance with the principles of liquid chromatography by passing the liquid through a chromatography column which contains the separation material according to the invention. The liquid can run through the column merely through its gravitational force or be pumped through by means of a pump. An alternative method is batch chromatography, in which the separation material is mixed with the liquid by stirring or shaking for as long as the target molecules or biopolymers need to be able to bind to the separation material. It is likewise possible to work in accordance with the principles of the chromatographic fluidised bed by introducing the liquid to be separated into, for example, a suspension comprising the separation material, where the separation material is selected so that it is suitable for the desired separation owing to its high density and/or a magnetic core.

If the chromatographic process is run in the bind and elute mode, the target molecule binds to the separation material. The separation material can subsequently be washed with a wash buffer, which preferably has the same ion strength and the same pH as the liquid in which the target molecule is brought into contact with the separation material. The wash buffer removes all substances which do not bind to the separation material. Further washing steps with other suitable buffers may follow without desorbing the target molecule. The desorption of the bound target molecule is carried out by changing the ion strength in the eluent and/or by changing the pH in the eluent and/or by changing the solvents. The target molecule can thus be obtained in a purified and concentrated form in the eluent. The target molecule usually has a purity of 70 percent to 99 percent, preferably 85 percent to 99 percent, particularly preferably 90 percent to 99 percent, after desorption.

It is also possible to use the above described bind and elute process to separate or purify more than one type of target molecule, whereby then the group of target molecules is bound to the separation material and separated from one or more impurities as described above.

However, if the chromatographic process is run in the flow-through mode, the target molecule or the group of different types of target molecules remains in the liquid, but other accompanying substances bind to the separation material. The target molecule is then obtained directly by collecting the column eluate in through-flow. It is known to the person skilled in the art how he has to adapt the conditions, in particular the pH and/or the conductivity, in order to bind a specific biopolymer to a separating material, or whether it is advantageous for the purification task not to bind the target molecule.

The present invention is preferably directed to the use of the above described separation materials for the separation and purification of glycoproteins and to a method for purification and/or separation of glycoproteins by liquid chromatography which comprises contacting the separation material with a sample comprising one or more glycoproteins preferably under acidic conditions.

Unexpectedly, we have found, that the ion exchange material according to the present invention can be used for the purification, separation or enrichment of glycoforms enabling an efficient glycan species separation at >10 mg glycoprotein/ml material capacities, where in a more preferred embodiment the capacity is between 10-80 mg/ml. Moreover, this innovative ion exchange material can be used in high conductivity>5 mS/cm, where in more preferred embodiment the conductivity is between 5-60 mS/cm.

Surprisingly, it was possible to separate and enrich glycan variants including high mannose containing variants, terminal mannose containing variants, fucose containing variants and no glycosylation containing variants preferably using a pH change from 4-7 to a pH above 9, preferably between 9 and 11, most preferred to pH 10 in gradient or step mode. Additionally, the application of this separation material showed significant economic advantages compared to affinity chromatography mode and enabled broader selectivity and enhanced performance compared to anion exchange mode.

Furthermore, the application is not limited to the separation of different glycan variant species, but can also be used to remove no glycosylation containing variants from the glycosylated ones.

Additionally, the application of this material is not limited to bind and elute applications, but can be used in a flow-through mode, resulting in higher mannose containing species or terminal mannose containing glycan variant adsorption on the ion exchange material using buffers having pH<6 and/or high conductivity (>20 mS/cm). Further, surprisingly only this ion exchange material, that primarily consists of amino acids covalently attached to the material, has the necessary selectivity for the glycan species, where in more preferred embodiment these amino acids are valine or leucine, including combinations and derivatives thereof, most preferred is leucine.

Further, the present invention provides a chromatography based glycoprotein purification step which can be regenerated and is applicable in a wide operation window, e.g. pH 3-10; conductivity 5-60 mS/cm.

In a preferred embodiment, the ion exchange material to be used in the present invention is incorporated into a chromatography column and used for glycoprotein purification processes in a bind and elute mode for separating glycan species.

In a preferred embodiment, the ion exchange material to be used in the present invention is incorporated into a chromatography column and used for glycoprotein purification processes in a bind and elute mode separating glycan species, where the operation window span is between pH 2-10, where in more preferred embodiment the pH is between 4-7.

In a preferred embodiment, the ion exchange material to be used in the present invention is incorporated into a chromatography column and used for glycoprotein purification processes in a bind and elute mode separating glycan species, where solvent pH elution is used to recover the bound components.

In a preferred embodiment, the ion exchange material to be used in the present invention is incorporated into a chromatography column and used for glycoprotein purification processes in a bind and elute mode for separating glycan species, where the binding window span is between 10 mg glycoprotein/ml material to 100 mg glycoprotein/ml material, where in more preferred embodiment the binding window span is between 20 mg glycoprotein/ml material to 80 mg glycoprotein/ml material.

In a preferred embodiment, the ion exchange material to be used in the present invention is incorporated into a chromatography column and used for glycoprotein purification processes in a bind and elute mode for separating glycan species, where the conductivity window span is between 5-60 mS/cm, where in the more preferred embodiment the conductivity range is between 15-35 mS/cm.

In another preferred embodiment, the ion exchange material to be used in the present invention is incorporated into a chromatography column and used for glycoprotein purification processes in a flow-through mode separating glycan species, where the low mannose containing species are in flow-through and higher mannose containing species bind to the separation material.

In another preferred embodiment, the ion exchange material to be used in the present invention is incorporated into a chromatography column and used for glycoprotein purification processes in a flow-through mode separating glycan species, where the non-hybrid species are in flow-through and hybrid (e.g. terminal mannose containing) species bind to the separation material.

In another preferred embodiment, the ion exchange material to be used in the present invention is incorporated into a chromatography column and used for glycoprotein purification processes in a flow-through mode separating glycan species, where the low fucosylation species are in flow-through and high fucosylation containing species bind to the separation material.

In another preferred embodiment the method of the present invention comprises a) applying a sample comprising a mixture of protein glycoforms whereby at least one of the glycoforms is a high mannose glycoform to a chromatography column comprising the ion exchange material to be used in the present invention b) separating and eluting the at least one high mannose glycoform in the flow-through c) eluting the bound glycoforms from the separation material, whereby the eluted glycoforms are reduced in high mannose glycoforms.

In another preferred embodiment the method of the present invention comprises a) applying a sample comprising a mixture of protein glycoforms whereby at least one of the glycoforms is a high mannose glycoform to a chromatography column comprising the ion exchange material to be used in the present invention whereby at least one high mannose glycoform, typically also other protein glycoforms, are bound to the separation material b) contacting the separation material with an elution buffer whereby at least one glycoform different from the high mannose glycoform is eluted while at least one high mannose glycoform remains bound to the separation material c) optionally contacting the separation material with a second elution buffer which typically differs from the first elution buffer and thereby eluting at least one high mannose glycoform.

In this embodiment, the eluate obtained in step b) is reduced in high mannose glycoforms compared to the sample applied in step a) and the eluate obtained in step c) is enriched. The mannose glycoforms separated in flow through or bind elute as described above are preferably antibodies having a differing degree of mannosylation or viruses and/or virus capsid carrying proteins with a differing degree of mannosylation.

In another preferred embodiment, the ion exchange material to be used in the method of the invention is incorporated into a chromatography column and used for glycoprotein purification processes in a flow-through or in bind elute mode for separating viruses and/or virus particles comprising glycoproteins form viruses and/or virus particles comprising other types of glycoproteins or no glycoproteins. Preferably the separation occurs based on differing amounts of mannose present in the glycan structure.

In another preferred embodiment the method of the present invention comprises a) applying a sample comprising a mixture of protein glycoforms whereby at least one of the glycoforms is a terminal mannose glycoform to a chromatography column comprising the ion exchange material to be used in the present invention whereby at least one terminal mannose glycoform, typically also other protein glycoforms, are bound to the separation material b) contacting the separation material with an elution buffer whereby at least one glycoform different from the terminal mannose glycoform is eluted while at least one terminal mannose glycoform remains bound to the separation material c) optionally contacting the separation material with a second elution buffer which typically differs from the first elution buffer and thereby eluting at least one terminal mannose glycoform.

In this embodiment, the eluate obtained in step b) is reduced in terminal mannose glycoforms compared to the sample applied in step a) and the eluate obtained in step c) is enriched. The terminal mannose glycoforms separated in flow through or bind elute as described above are preferably antibodies having a differing degree of mannosylation or viruses and/or virus capsid carrying proteins with a differing degree of mannosylation.

In another preferred embodiment, the ion exchange material to be used in the method of the invention is incorporated into a chromatography column and used for glycoprotein purification processes in a flow-through or in bind elute mode for separating viruses and/or virus particles comprising glycoproteins form viruses and/or virus particles comprising other types of glycoproteins or no glycoproteins. Preferably the separation occurs based on differing amounts of terminal mannose present in the glycan structure.

In another preferred embodiment the method of the present invention comprises a) applying a sample comprising a mixture of protein glycoforms whereby at least one of the glycoforms is a fucose carrying glycoform to a chromatography column comprising the separation material to be used in the present invention whereby at least one fucose carrying glycoform, typically also other protein glycoforms, are bound to the separation material b) contacting the separation material with an elution buffer whereby at least one glycoform different from the no fucose carrying glycoform is eluted while at least one fucose carrying glycoform remains bound to the separation material c) optionally contacting the separation material with a second elution buffer which typically differs from the first elution buffer and thereby eluting at least one no fucose carrying glycoform.

In this embodiment, the eluate obtained in step b) is reduced in no fucose carrying glycoforms compared to the sample applied in step a) and the eluate obtained in step c) is enriched. The fucose carrying glycoforms separated in flow through or bind elute as described above are preferably antibodies having a differing degree of fucosylation or viruses and/or virus capsid carrying proteins with a differing degree of fucosylation.

In another preferred embodiment, the ion exchange material to be used in the method of the invention is incorporated into a chromatography column and used for glycoprotein purification processes in a flow-through or in bind elute mode for separating viruses and/or virus particles comprising glycoproteins form viruses and/or virus particles comprising other types of glycoproteins or no glycoproteins. Preferably the separation occurs based on differing amounts of fucose present in the glycan structure.

In another preferred embodiment the method of the present invention comprises
a) applying a sample comprising a mixture of protein with glycans and without glycans whereby at least one of the proteins with glycans, the protein glycoform, is bound to a chromatography column comprising the separation material to be used in the present invention
b) contacting the separation material with an elution buffer whereby at least one protein with glycans is eluted while at least one without glycans remains bound to the separation material
c) optionally contacting the separation material with a second elution buffer which typically differs from the first elution buffer and thereby eluting at least one without glycans.

In this embodiment, the eluate obtained in step b) is enriched in glycoforms carrying protein compared to the sample applied in step a) and the eluate obtained in step c) is reduced. The glycoforms separated in flow through or bind elute as described above are preferably antibodies having a differing degree of glycosylation or viruses and/or virus capsid carrying proteins with a differing degree of glycosylation.

In another preferred embodiment, the ion exchange material to be used in the method of the invention is incorporated into a chromatography column and used for glycoprotein purification processes in a flow-through or in bind elute mode for separating viruses and/or virus particles comprising glycoproteins form viruses and/or virus particles comprising other types of glycoproteins or no glycoproteins. Preferably the separation occurs based on differing amounts of glycosylation present in the glycan structure.

In another preferred embodiment, the ion exchange material to be used in the present invention is incorporated into a chromatography column and used for glycoprotein purification processes in a flow-through mode separating glycan species, where the glycosylation containing proteins are in flow-through and not glycosylated proteins bind to the separation material.

In a preferred embodiment, ion exchange material can be sized to various particle sizes ranging from 1-200 μm, whereby in a more preferred embodiment the average particle size is between 20-63 μm.

In a preferred embodiment, the ion exchange material according to the present invention can have various pore sizes ranging from 4-1500 nm, whereby in a more preferred embodiment the average pore size is between 10-120 nm, and in a most preferred embodiment the average pore size is between 40-110 nm.

The method of the present invention is extremely flexible. The chromatography mode (bind-elute or flow-through) can be applied as suitable as well as the conditions can be varied in the above mentioned broad ranges. In addition, also the target molecule can be varied. As discussed above, in any case the sample comprises at least one protein glycoform. But the target molecule can either be a protein glycoform, a group of different protein glycoforms or a non-glycosylated protein. Typically, in the method of the invention, at least one protein glycoform binds to the separation material but this protein glycoform need not necessarily be the target molecule. It might be the target molecule, but the target molecule can also be another protein glycoform or a non-glycosylated protein that also binds to the separation material or is in the flow through. As the process of the invention allows for the separation of different protein glycoforms as well as of glycosylated and non-glycosylated proteins, the target molecule can be defined as need be.

The present invention is further illustrated by the following figures and examples, however, without being restricted thereto.

The entire disclosure of all applications, patents, and publications cited above and below as well as of the corresponding EP patent application 19184130.3, filed Jul. 7, 2019, are hereby incorporated by reference.

Examples

The following examples represent practical applications of the invention.

1. Synthesis of Separation Material

For the preparation of the monomers to be used for the grafting from process the amino acids, e.g. valine, leucine or alanine, are dissolved in VE water and the pH is adjusted to a pH above 13 by adding NaOH (32%). At a temperature between 0-5° C. the acrylic compound like acrylic acid chloride or acrylic acid is added and the mixture is stirred for one hour. The reaction scheme for valine and leucine with acrylic acid chloride is shown in FIG. 2 and FIG. 3.

Then the pH is adjusted to about pH 2.2 by adding nitric acid. Afterwards the OH containing base material is added, e.g. Eshmuno® particles.

Polymerization is started by adding Cerium (IV) nitrate. The reaction takes place for 4 hours at 30-50° C.

After the polymerization reaction the non-reacted components and starter are removed by extensive washing using acidic, basic and solvent mixtures at room or elevated temperatures.

2. Rituximab® with High Mannose Glycan Form Separation

The ion exchange material as prepared according to Example 1 (e.g. with the average particle size between 20-63 μm, the average pore size between 40-110 nm and an ionic density between 400-900 μeq/g) was evaluated for its ability to separate high mannose containing species of commercially available drug Rituximab®. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having pH of 4.75 and 250 mM NaCl. The buffer solution contained a combination of salts such as sodium dihydrogen phosphate, TRIS, and glycine to obtain the pH of 4.5. The same solution was used to dilute the Rituximab® sample till 4.8 mg/ml concentration. This solution was loaded on the prepared chromatographic column till 20 mg Rituximab® loading was reached for 1 ml resin. These steps and the following steps were performed at 150 cm/h buffer velocity. After loading 20 mg/ml Rituximab®, the chromatographic column was washed with pH 4.75 buffer solution and then eluted using gradient elution with buffer having pH of 8.5 and 250 mM NaCl. This elution buffer was prepared using different salts such as sodium dihydrogen phosphate, TRIS, and glycine. The conductivity and pH values were traced during the experimental set-up, showing that the Rituximab® elution from the column was achieved due to the pH change during the gradient elution. The sample elution was fractionated and obtained fractions were evaluated of line using a LC-MS method for the glycan specie identification (FIG. 4).

Figure 5:
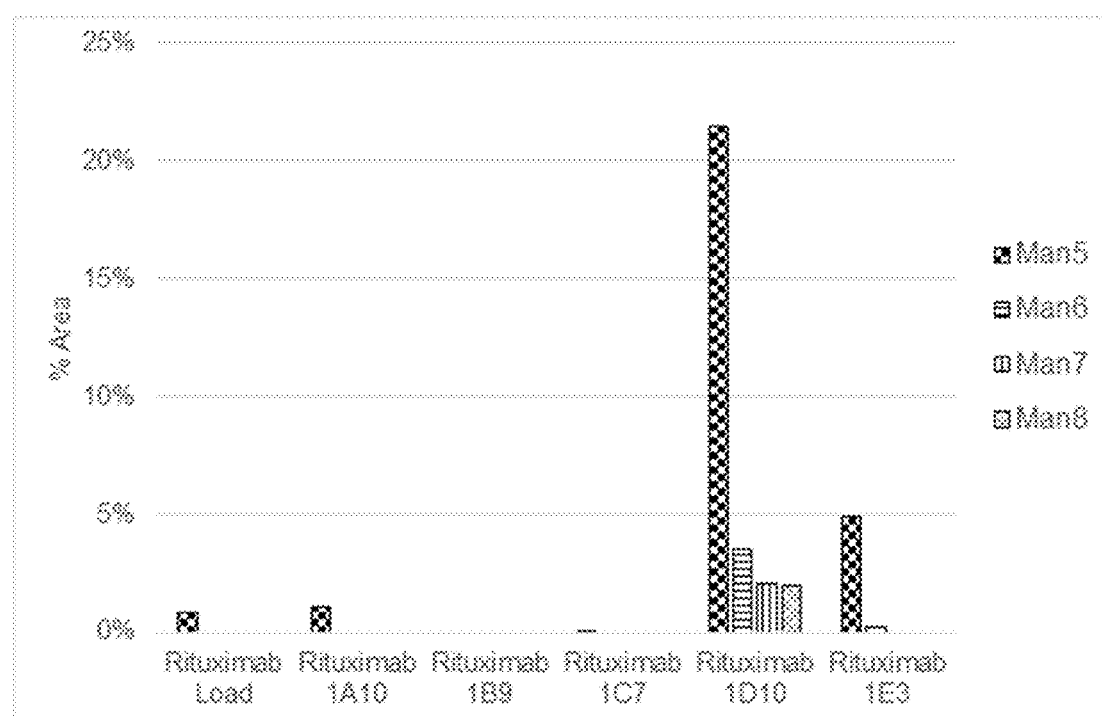
FIG. 5 shows analytical results of the sample fraction characterization using a LC-MS analytical method displayed in quantitative area of analyzed elution fractions (1A10 to 1E3), including loaded glycoprotein (load) at 20 mg glycoprotein/ml CV loading and 250 mM NaCl.

The analytical evaluation using LC-MS analytical method of collected fractions is displayed in the FIG. 5, showing that the main glycoprotein elution peak, further characterized with representative 1B9 and 1C7 fractions, did not contain any high mannose glycan variants. Most of the high mannose glycan variants eluted at higher pH, further characterized with representative 1D10 and 1E3 fractions (FIG. 5).

Figure 4:
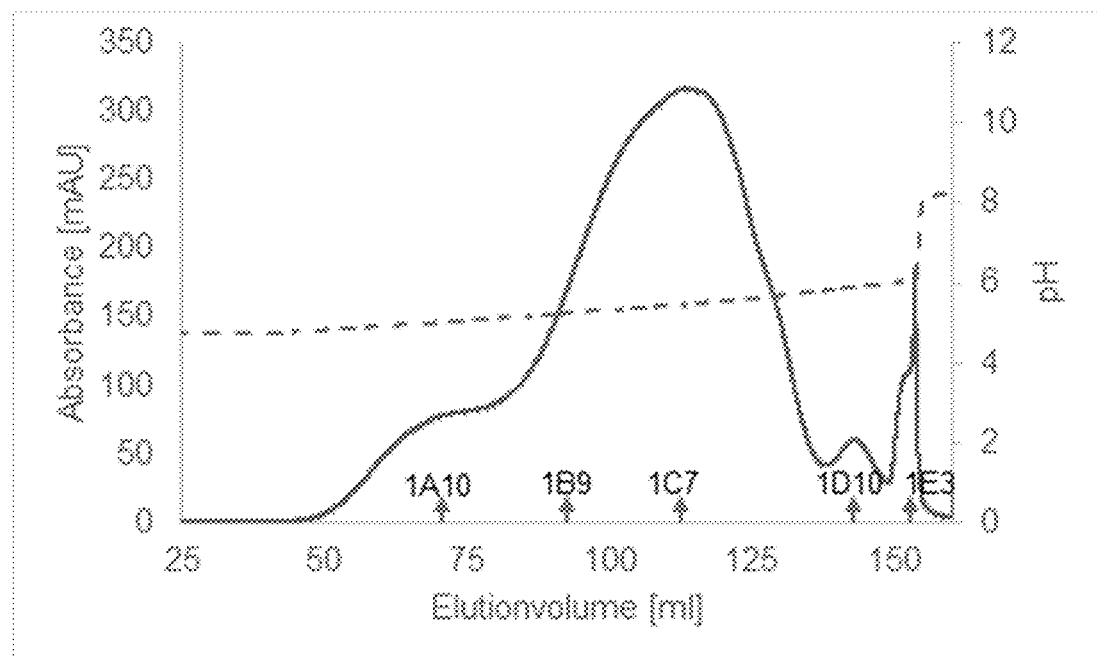
FIG. 4 shows the elution peak of the bound glycoprotein on the separation matrix at 20 mg/ml CV loading and 250 mM NaCl. UV adsorption signal trace in solid line and pH signal trace in dashed line.

As shown in FIG. 4 while using a linear pH gradient elution the separation/enrichment of the high mannose containing glycan species is possible. In the main glycoprotein containing fractions (e.g. 1B9 and 1C7) no high mannose variant was detected. All high mannose containing variants eluted in a separate fraction (e.g. 1D10).

3. Erbitux® with High Mannose Glycan form Separation in Wide Application Window Within 200 mM to 600 mM Sodium Sulfate The ion exchange material as prepared according to Example 1 (e.g. with the average particle size between 20-63 µm, the average pore size between 40-110 nm and an ionic density between 400-900 µeq/g) was evaluated for its ability to separate high mannose containing species of commercially available drug Erbitux®. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having a pH of 4.5 and 250 mM NaCl. The buffer solution contained a combination of salts such as sodium dihydrogen phosphate, TRIS, and glycine to obtain the pH of 4.5. The pre-purified Erbitux® sample was loaded on the prepared chromatographic column till 5 mg pre-purified Erbitux® loading was reached for 1 ml resin. These steps and the following steps were performed at 150 cm/h buffer velocity. After loading 5 mg/ml pre-purified Erbitux®, the chromatographic column was washed with pH 4.5 buffer solution and varying amounts of $Na_2SO_4$. The amount of $Na_2SO_4$ was varied between 200 and 600 mM. The column was then eluted using gradient elution with buffer having a pH of 8.5 and corresponding $Na_2SO_4$ amounts. This elution buffer was prepared using different salts such as sodium dihydrogen phosphate, TRIS, and glycine. The conductivity and pH values were traced during the experimental set-up, showing that the Erbitux® elution from the column was achieved due to the pH change during the gradient elution. In Table 1 are displayed the main peak and high mannose containing peak elution maximum values in corresponding pH.

| $Na_2SO_4$ amount in used wash and elution buffers (mM) | Peak elution pH values | |
| --- | --- | --- |
| | Main peak | High mannose containing peak |
| 200 | 5.38 | 5.86 |
| 300 | 5.17 | 5.74 |
| 400 | 5.10 | 5.79 |
| 500 | 5.11 | 5.80 |
| 600 | 5.16 | 5.94 |

Table 1 shows the main peak and high mannose containing peak elution maximum values in corresponding pH.

As shown in Table 1 while using a linear pH gradient elution the separation/enrichment of the high mannose containing glycan species was possible in a wide range of conductivity. Fractions with high mannose containing variants eluted throughout the whole investigated range at higher pH values in comparison to no high mannose containing glycan species.

4. Rituximab® with Hybrid Glycan Form Separation

The ion exchange material as prepared according to Example 1 (e.g. with the average particle size between 20-63 µm, the average pore size between 40-110 nm and an ionic density between 400-900 µeq/g) was evaluated for its ability to separate hybrid glycan species of commercially available drug Rituximab®. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having a pH of 4.75 and 250 mM NaCl. The buffer solution contained a combination of salts such as sodium dihydrogen phosphate, TRIS, and glycine to obtain the pH of 4.5. The same solution was used to dilute the Rituximab® sample till 4,8 mg/ml concentration. This solution was loaded on the prepared chromatographic column till 20 mg Rituximab® loading was reached for 1 ml resin. These steps and the following steps were performed at 150 cm/h buffer velocity. After loading 20 mg/ml Rituximab®, the chromatographic column was washed with pH 4.75 buffer solution and then eluted using gradient elution with buffer having a pH of 8.5 and 250 mM NaCl. This elution buffer was prepared using different salts such as sodium dihydrogen phosphate, TRIS, and glycine. The conductivity and pH values were traced during the experimental set-up, showing that the Rituximab® elution from the column was achieved due to the pH change during the gradient elution. The sample elution was fractionated and obtained fractions were evaluated of line using a LC-MS method for the glycan specie identification (FIG. 7).

Figure 7:
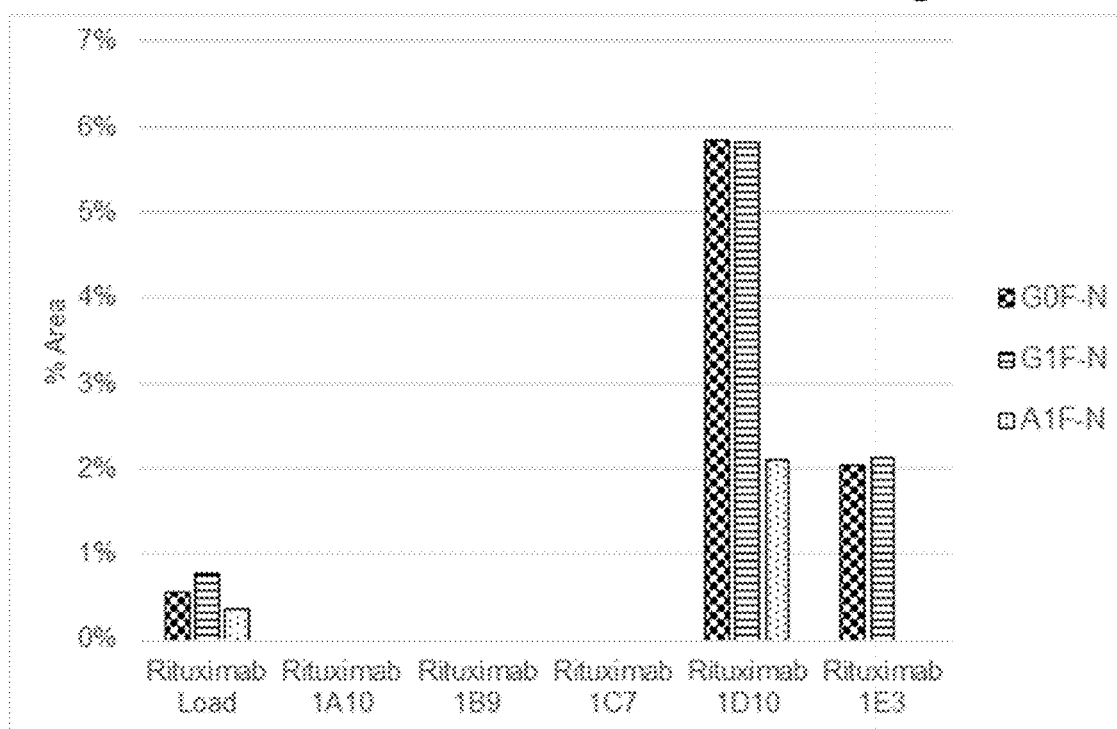
FIG. 7 shows analytical results of the sample fraction characterization using a LC-MS analytical method displayed in quantitative area of analyzed elution fractions (1A10 to 1E3), including loaded glycoprotein (load) at 20 mg glycoprotein/ml CV loading and 250 mM NaCl.

The analytical evaluation using a LC-MS analytical method of the collected fractions is displayed in FIG. 7, showing that the main glycoprotein elution peak, further characterized with representative 1B9 and 1C7 fractions, did not contain any hybrid glycan variants (e.g. terminal mannose containing). Most of the hybrid glycan variants eluted at higher pH, further characterized with representative 1D10 and 1E3 fractions (FIG. 7).

Figure 6:
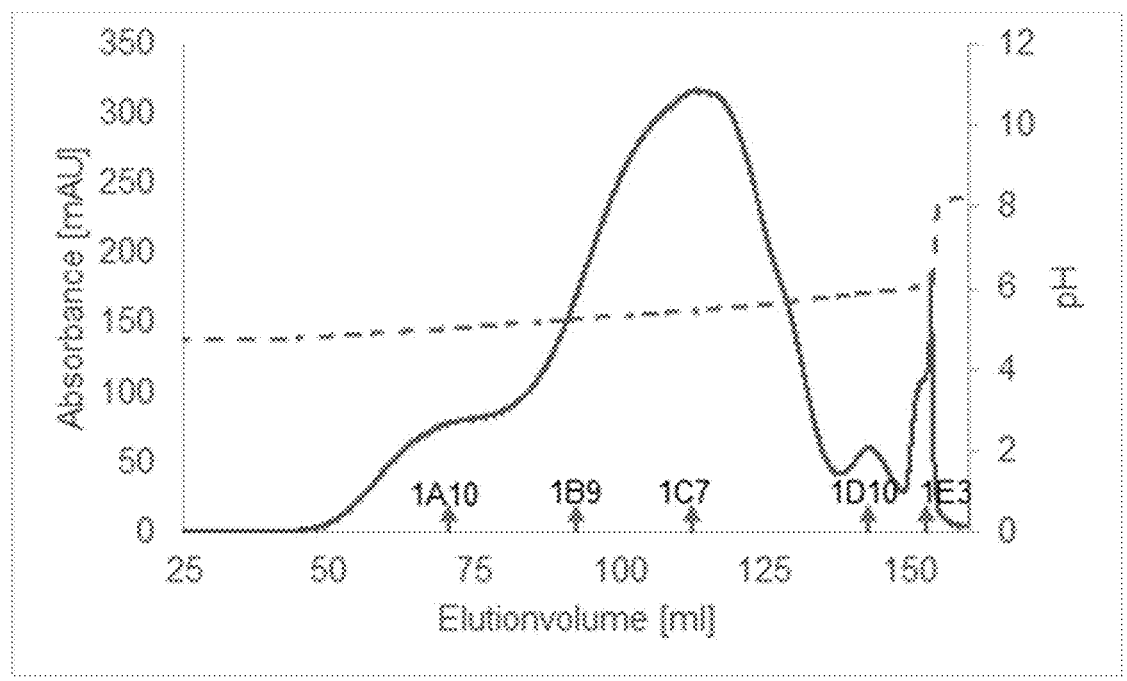
FIG. 6 shows the elution peak of the bound glycoprotein on the separation material at 20 mg/ml CV loading and 250 mM NaCl. UV adsorption signal trace in solid line and pH signal trace in dashed line.

As shown in FIG. 6 and FIG. 7 while using a linear pH gradient elution the separation/enrichment of hybrid glycan species is possible. In the main glycoprotein containing fractions (e.g. 1B9 and 1C7) no hybrid glycan variant was detected. All hybrid glycan variants eluted in separate fractions (e.g. 1D10 and 1E3).

5. mAb05 with Hybrid Glycan Form Separation

The ion exchange material as prepared according to Example 1 (e.g. with the average particle size between 20-63 μm, the average pore size between 40-110 nm and an ionic density between 400-900 μeq/g) was evaluated for its ability to separate hybrid glycan species of mAb05. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having a pH of 4.75 and 250 mM NaCl. The buffer solution contained a combination of salts such as sodium dihydrogen phosphate, TRIS, and glycine to obtain the pH of 4.75. The same solution was used to dilute the mAb05 sample till 5 mg/ml concentration. This solution was loaded on the prepared chromatographic column till 30 mg mAb05 loading was reached for 1 ml resin. These steps and the following steps were performed at 150 cm/h buffer velocity. After loading 30 mg/ml mAb05, the chromatographic column was washed with pH 4.75 buffer solution and then eluted using gradient elution with buffer having a pH of 8.5 and 250 mM NaCl. This elution buffer was prepared using different salts such as sodium dihydrogen phosphate, TRIS, and glycine. The conductivity and pH values were traced during the experimental set-up, showing that the mAb05 elution from the column was achieved due to the pH change during the gradient elution. The sample elution was fractionated and obtained fractions were evaluated of line using LC-MS method for the glycan specie identification (FIG. 9).

Figure 9:
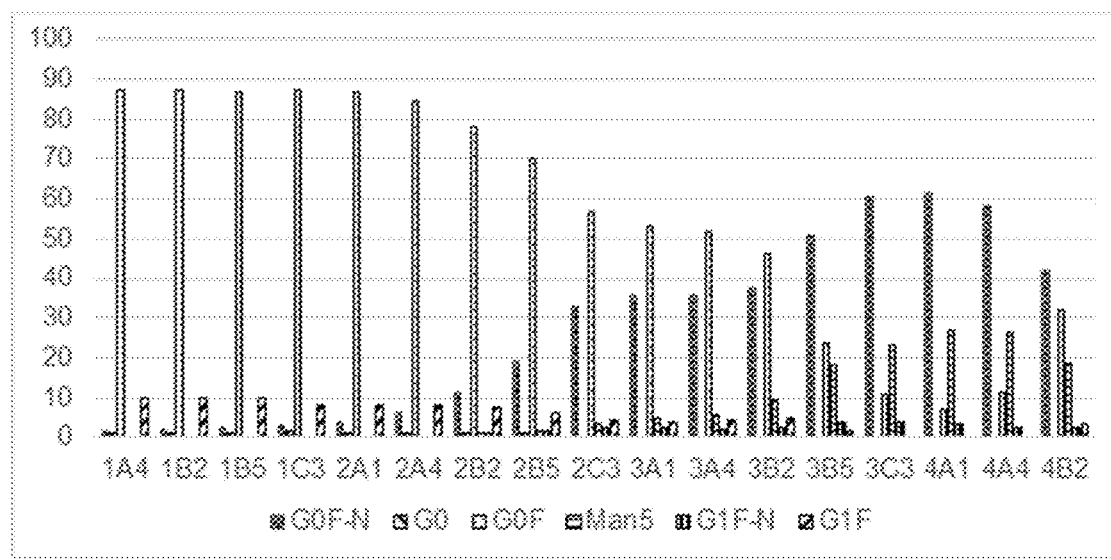
FIG. 9 shows analytical results of the sample fraction characterization using a LC-MS analytical method displayed in quantitative area of analyzed elution fractions (1A4 to 4B2).

The analytical evaluation using LC-MS analytical method of collected fractions is displayed in the FIG. 9, showing that the first elution fractions 1A4-2A4, did not contain any hybrid glycan variants (e.g. terminal mannose containing G0F-N and G1F-N). Most of the hybrid glycan variants eluted at higher pH, further characterized with representative 3B5 to 4B2 fractions (FIG. 9). In addition to hybrid forms the mannose 5 containing glycan variant was eluted at higher pH as well.

Figure 8:
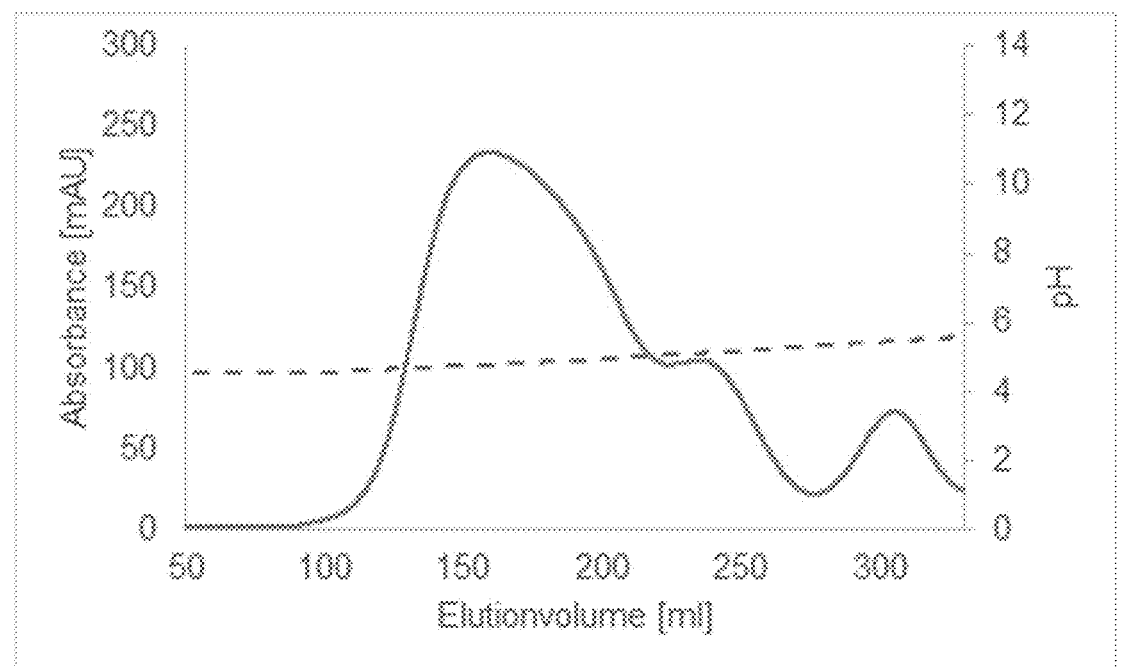
FIG. 8 shows the elution peak of the bound glycoprotein (e.g. mAb05) on the separation material at 30 mg/ml CV loading and 250 mM NaCl. UV adsorption signal trace in blue line.

As shown in FIG. 8 while using a linear pH gradient elution the separation/enrichment of hybrid glycan species is possible. In the main glycoprotein containing fractions (e.g. 1A4 to 2A4) no hybrid glycan variants were detected. All hybrid glycan variants eluted at higher pH values (e.g. 3B5 to 4B2).

Moreover, analytical size exclusion chromatography was used to characterize the obtained fractions and to monitor the level of fragmentation or aggregation. The results show less then 1% aggregate presence in the used sample or obtained fractions (Table 2).

|  | HMW % | Monomer % | LMW % | Concentration mAb ma/ml |
|---|---|---|---|---|
| Load | 0.59 | 99.04 | 0.37 | 5.825 |
| 2A1 | 0.00 | 100.00 | 0.00 | 0.950 |
| 2C2 | 0.43 | 99.57 | 0.00 | 0.570 |
| 3C5 | 0.75 | 99.25 | 0.00 | 0.413 |

Table 2 shows the analytical size exclusion chromatography results displayed for the obtained fractions in area and % for the fragmented or aggregated species. All fractions were >99% pure.

6. mAb05 with Fucosylated, Non Fucosylated Form Separation

Figure 10:
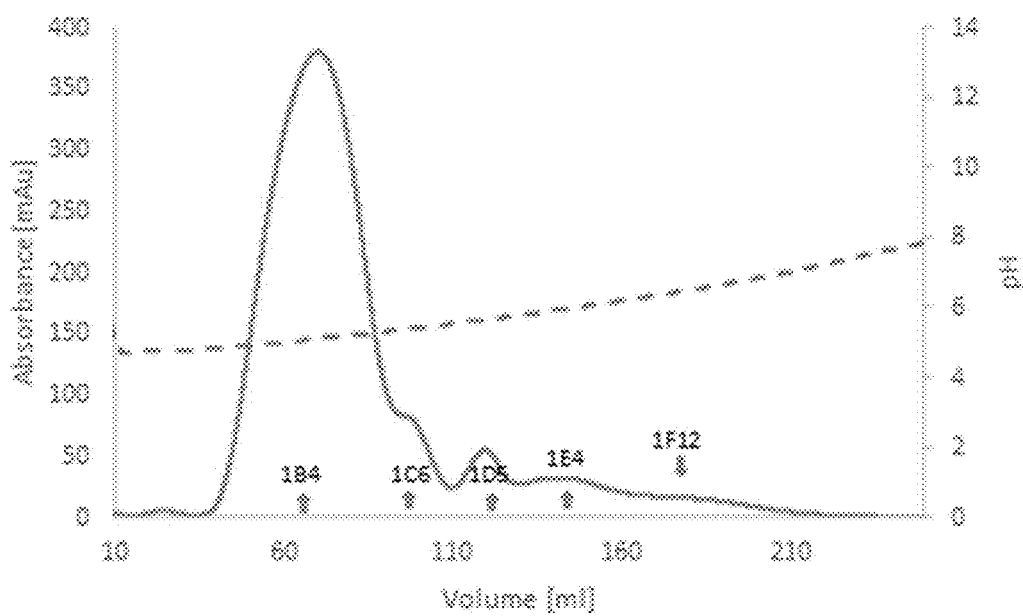
FIG. 10 shows the elution peak of the bound glycoprotein (e.g. mAb05) on the separation material at 30 mg/ml CV loading and 200 mM NaCl. UV adsorption signal trace in solid line and pH in dashed line.

The ion exchange material as prepared according to Example 1 (e.g. with the average particle size between 20-63 μm, the average pore size between 40-110 nm and an ionic density between 400-900 μeq/g) was evaluated for its ability to separate fucosylated and non fucosylated glycan species of mAb05. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having a pH of 4.75 and 200 mM NaCl. The buffer solution contained a combination of salts such as sodium dihydrogen phosphate, TRIS, and glycine to obtain the pH of 4.75. The same solution was used to dilute the mAb05 sample till 5 mg/ml concentration. This solution was loaded on the prepared chromatographic column till 30 mg mAb05 loading was reached for 1 ml resin. These steps and the following steps were performed at 150 cm/h buffer velocity. After loading 30 mg/ml mAb05, the chromatographic column was washed with pH 4.75 buffer solution and then eluted using gradient elution with buffer having a pH of 8.5 and 200 mM NaCl. This elution buffer was prepared using different salts such as sodium dihydrogen phosphate, TRIS, and glycine. The conductivity and pH values were traced during the experimental set-up, showing that the mAb05 elution from the column was achieved due to the pH change during the gradient elution (FIG. 10). The sample elution was fractionated and obtained fractions were evaluated of line using a LC-MS method for the glycan species identification (Table 3).

The analytical evaluation using a LC-MS analytical method of the collected fractions is displayed in the Table 3, showing that the first elution fractions 1B4-1D5, did contain less non fucosylated forms (G0 and G1) compared to (G0F and G1F) than the loaded glycoprotein. A higher amount of fucosylated glycan variants (G0F and G1F) eluted at higher pH, further characterized with representative 1E4 and 1F12 fractions (Table 3). Additionally, the mannose 5 containing glycan variant was eluted at higher pH as well.

| Component name | Load % Area | 1B4 % Area | 1C6 % Area | 1D5 % Area | 1E4 % Area | 1F12 % Area |
|---|---|---|---|---|---|---|
| (G0-N) | 1.88% |  | 12.11% | 5.80% | 9.10% | 3.96% |
| (G0F-N) | 1.01% | 0.39% | 3.75% | 2.54% | 3.53% | 2.50% |
| (G0) | 31.38% | 35.50% | 25.95% | 24.00% | 17.50% | 20.80% |
| (G0F) | 41.29% | 41.90% | 33.85% | 31.74% | 30.29% | 42.50% |
| (G1F-N) | 0.14% |  |  | 0.45% | 0.48% | 0.26% |
| (Man5) | 2.09% |  | 4.37% | 15.45% | 21.21% | 7.38% |
| (G1) | 5.72% | 6.21% | 6.27% | 4.96% | 4.61% | 4.37% |
| (G1F) | 14.68% | 14.99% | 10.41% | 11.50% | 8.61% | 14.79% |

-continued

| Component name | Load % Area | 1B4 % Area | 1C6 % Area | 1D5 % Area | 1E4 % Area | 1F12 % Area |
|---|---|---|---|---|---|---|
| (G2) | 0.35% | | | 0.23% | | 0.50% |
| (Man6) | 0.18% | | | 1.50% | 1.91% | 0.80% |
| (G2F) | 1.06% | 1.00% | | | | 0.56% |
| (Man8) | | | | | 0.95% | |
| Deviation G0F – G0 | 9.92% | 6.40% | 7.90% | 7.74% | 12.79% | 21.70% |
| Deviation G1F – G1 | 8.97% | 8.78% | 4.14% | 6.54% | 4.01% | 10.41% |

Table 3 shows the analytical results of the sample fraction characterization using a LC-MS analytical method displayed in quantitative area of analyzed elution fractions (1B4 to 1F12).

As shown in FIG. 10 and Table 3 while using a linear pH gradient elution the separation/enrichment of non fucosylated glycan species is possible. In the main glycoprotein containing fractions (e.g. 1B4 to 1D5) less fucosylated glycan variants were detected. More fucosylated glycan variants eluted at higher pH values (e.g. 1E4 to 1F12).

7. Separation of Native and Deglycosylated Rituximab®

The ion exchange material as prepared according to Example 1 (e.g. with the average particle size between 20-63 µm, the average pore size between 40-110 nm and an ionic density between 400-900 µeq/g) was evaluated for its ability to separate a glycosylated and a non-glycosylated Rituximab®. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having a pH of 4.75 and 150 mM NaCl. The buffer solution contained a combination of salts such as sodium dihydrogen phosphate, TRIS, and glycine to obtain the pH of 4.75. The same solution was used to dilute the native and deglycosylated Rituximab® sample till 4 mg/ml concentration. This solution was loaded on the prepared chromatographic column till 1 mg Rituximab® loading was reached for 1 ml resin. These steps and the following steps were performed at 150 cm/h buffer velocity. After loading 1 mg/ml Rituximab®, the chromatographic column was washed with pH 4.75 buffer solution and then eluted using gradient elution with buffer having a pH of 8.5 and 150 mM NaCl. This elution buffer was prepared using different salts such as sodium dihydrogen phosphate, TRIS, and glycine. The conductivity and pH values were traced during the experimental set-up, showing that the Rituximab® elution from the column was achieved due to the pH change during the gradient elution.

For preparing the sample, the Rituximab® was partly deglycosylated using Endoglycosydase digest.

The partly deglycosylated and native Rituximab® where both loaded in two different applications and the retention time compared (FIG. 11).

The elution profile of the native glycoprotein (e.g. Rituximab®) in a linear pH gradient shows a lower elution pH for the native glycosylated protein. The deglycosylated part of the glycoproteins elutes at a higher pH of the gradient.

As shown in FIG. 11 while using a linear pH gradient elution the separation/enrichment of deglycosylated and native glycoprotein is possible.

8. mAb05 with High Mannose Glycan Form Separation in Flow Through Mode

The ion exchange material as prepared according to Example 1 (e.g. with the average particle size between 20-63 µm, the average pore size between 40-110 nm and an ionic density between 400-900 µeq/g) was evaluated for its ability to separate high mannose glycan species of mAb05 in flow through mode. The ion exchange material was packed in a chromatographic column of 5×100 mm dimensions with asymmetry between 0.8-1.2 and >3000-plates/m. After packing the ion exchange material, the obtained chromatographic column was cleaned with 1 M NaOH solution for 30 minutes and preequilibrated with loading buffer solution having a pH of 4.75 and 400 mM NaCl. The buffer solution contained a combination of salts such as sodium dihydrogen phosphate, TRIS, and glycine to obtain the pH of 4.75. The same solution was used to dilute the mAb05 sample till 4.8 mg/ml concentration. This solution was loaded on the prepared chromatographic column till 10 mg mAb05 loading was reached for 1 ml resin. These steps and the following steps were performed at 150 cm/h buffer velocity. After loading 10 mg/ml mAb05, the chromatographic column was washed with pH 4.75 buffer solution and then eluted using gradient elution with buffer having a pH of 8.5 and 400 mM NaCl. This elution buffer was prepared using different salts such as sodium dihydrogen phosphate, TRIS, and glycine. The conductivity and pH values were traced during the experimental set-up, showing that the high mannose mAb05 glycovariants elution from the column was achieved due to the pH change during the gradient elution. Whereas the glycovariants with no mannose do not bind on the column and are in the flow through. The flow through and sample elution was fractionated and obtained fractions were evaluated using a LC-MS method for the glycan specie identification (Table 4).

| | Load | 1F8 | 1H9 |
|---|---|---|---|
| (G0) | 31.38% | 33.29% | 9.64% |
| (G0F) | 41.29% | 40.84% | 13.19% |
| (Man5) | 2.09% | 0.18% | 33.09% |
| (G1) | 5.72% | 7.03% | 3.59% |
| (G1F) | 14.68% | 15.53% | 5.25% |
| (Man6) | 0.18% | | 4.35% |
| (Man7) | | | 2.58% |
| (Man8) | | | 1.27% |

Table 4 shows the analytical evaluation using a LC-MS analytical method of the collected fractions. Showing that the flow through fraction 1F8, did contain<1% mannose containing glycovariants. Most of the mannose containing glycovariants eluted at higher pH, further characterized with representative fraction 1H9 (Table 4).

As shown in FIG. 12 while using a linear pH gradient elution the separation/enrichment of low mannose containing glycan species in flow through is possible. In the bound fractions (e.g. 1H9) high mannose glycan variants was detected. High mannose glycan variants eluted at higher pH values (e.g. 1H9).

9. Spike S1 Protein of SARS-CoV-2 Separation in Bind-Elute Mode

The ion exchange material as prepared according to Example 1 (e.g. with the average particle size between 20-63 µm, the average pore size between 40-110 nm and an ionic density between 400-900 µeq/g) was evaluated for its ability to bind the Spike S1 protein of SARS-CoV-2. The ion exchange material was packed in a chromatographic column of 5×100 mm dimensions with asymmetry between 0.8-1.2 and >3000 plates/m. After packing the ion exchange material, the obtained chromatographic column was cleaned with 1 M NaOH solution for 30 minutes and preequilibrated with loading buffer solution having pH of 4.75 and 250 mM NaCl. The buffer solution contained a combination of salts such as sodium dihydrogen phosphate, TRIS, and glycine to obtain the pH of 4.75. The same solution was used to reconstitute the S1 protein sample till 0.6 mg/ml concentration. This solution was loaded on the prepared chromatographic column till 1 mg S1 protein loading was reached for 1 ml resin. These steps and the following steps were performed at 150 cm/h buffer velocity. After loading 1 mg/ml S1 protein, the chromatographic column was washed with pH 4.75 buffer solution and then eluted using gradient elution with buffer having pH of 10.5 and 250 mM NaCl. This elution buffer was prepared using different salts such as sodium dihydrogen phosphate, TRIS, and glycine. The conductivity and pH values were traced during the experimental set-up, showing that the S1 protein elution from the column was achieved due to the pH change during the gradient elution. The sample elution was fractionated and obtained fractions were evaluated of line using an analytical HIC method for the protein identification (FIG. 13).

The analytical evaluation using analytical HIC method of collected fractions is displayed in the FIG. 14, showing that the main elution peak (dashed line), further characterized with representative 106 fraction, did contain only S1 protein (solid line). (FIG. 14).

As shown in FIG. 13 while using a linear pH gradient elution the binding/elution of the SARS-CoV-2 Spike S1 protein is possible. The elution peak only contains S1 protein.

10. mAb03 with High Mannose Glycan Form Separation in Flow Through Mode

The ion exchange material as prepared according to Example 1 (e.g. with the average particle size between 20-63 µm, the average pore size between 40-110 nm and an ionic density between 400-900 µeq/g) was evaluated for its ability to separate high mannose glycan species of mAb03 in flow through mode. The ion exchange material was packed in a chromatographic column of 5×100 mm dimensions with asymmetry between 0.8-1.2 and>3000-plates/m. After packing the ion exchange material, the obtained chromatographic column was cleaned with 1 M NaOH solution for 30 minutes and preequilibrated with loading buffer solution having a pH of 5.12 and 250 mM NaCl. The buffer solution contained a combination of salts such as sodium dihydrogen phosphate, TRIS, and glycine to obtain the pH of 5.12. The same solution was used to dilute the mAb03 sample till 5.0 mg/ml concentration. This solution was loaded on the prepared chromatographic column till 100 mg mAb03 loading was reached for 1 ml resin. These steps and the following steps were performed at 150 cm/h buffer velocity. After loading 100 mg/ml mAb03, the chromatographic column was washed with pH 5.12 buffer solution and then eluted using gradient elution with buffer having a pH of 8.5 and 250 mM NaCl. This elution buffer was prepared using different salts such as sodium dihydrogen phosphate, TRIS, and glycine. The conductivity and pH values were traced during the experimental set-up, showing that the high mannose mAb03 glycovariants elution from the column was achieved due to the pH change during the gradient elution. Whereas the glycovariants with no mannose do not bind on the column and are in the flow through. The flow through was fractionated and obtained fractions were evaluated for the high mannose specie quantity (Table 5).

| Loading of mAb03 (mg/ml column volume) | High mannose specie quantity (%) |
| --- | --- |
| 25.5 | 0.53 |
| 35.7 | 0.52 |
| 45.8 | 0.51 |
| 56.0 | 0.65 |
| 66.2 | 0.91 |
| 76.4 | 1.20 |
| 86.6 | 1.49 |
| 96.8 | 1.82 |
| 100.0 | 2.06 |

Table 5 shows the analytical evaluation of the commulative high mannose specie amount the collected fractions after certain mAb03 break through. The starting concentration of high mannose specie was 7.68%. Thereby it is shown, that 66.2 mg of flown through mAb03 sample, did contain<1% high mannose containing glycovariants.

11. Gammanorm® Static Binding Capacity

The static binding capacity of Gammanorm® was measured using material prepared of the hexafluoro-valine used for the grafting. Hexafluoro-valine was dissolved in VE water and the pH was adjusted to a pH above 13 by adding NaOH (32%). At a temperature between 0-5° C. the acrylic compound like acrylic acid chloride or acrylic acid was added and the mixture was stirred for one hour. Then the pH was adjusted to about pH 2.2 by adding nitric acid. Afterwards the OH containing base material was added, e.g. Eshmuno® particles. Polymerization was started by adding Cerium (IV) nitrate. The reaction took place for 4 hours at 30-50° C. An exact amount of such material was soaked in the solution containing 5 mg/ml Gammanorm at pH 5.0 and various amounts of NaCl. After incubation for 4 hours, the material was removed and remaining Gammanorm® amount in solution was measured thereby estimating the amount of the bound Gammanorm®. The measured static binding capacities were as follows:

at 0 mM NaCl-64.5 mg Gammanorm®/ml hexafluoro-valine grafted material; at 30 mM NaCl-50.9 mg Gammanorm®/ml hexafluoro-valine grafted material; at 75 mM NaCl-50 mg Gammanorm®/ml hexafluoro-valine grafted material was bound.

The invention claimed is:

1. A method for the chromatographic purification and/or separation of protein glycoforms by contacting a sample comprising the protein glycoforms with a separation material comprising of a base matrix to the surfaces of which polymer chains are covalently bonded, characterised in that
   the polymer chains comprise end groups —N(Y)—R3 with Y being independently from each other H or $CH_3$, and
   R3 being —CHCOOMR4
   with R4 being C1 to C4 alkyl or C1 to C4 perfluoroalkyl and M being H, Na, K, or $NH_4$.
2. The method of claim 1 comprising the steps of
   a) contacting the sample comprising the protein glycoforms with said separation material whereby one or more of the protein glycoforms are bound to the separation material;

b) optionally washing the separation material; and
c) contacting the separation material with an elution buffer under conditions in which bound protein glycoforms elute from the separation material.

3. The method according to claim 2, characterized in that the method further includes recovering protein glycoforms which flow through the separation material in step a).

4. The method according to claim 2, characterized in that the elution buffer has a pH higher than a loading buffer used for contacting the sample with the separation material in step a).

5. The method according to claim 2, characterized in that, in step a), the sample has a conductivity of between 5 and 60 mS/cm.

6. The method according to claim 1, characterized in that the sample comprises one or more of the following: high mannose protein glycoforms; terminal mannose protein glycoforms; fucosylated and non-fucosylated protein glycoforms; glycosylated and non-glycosylated proteins.

7. The method according to claim 1, characterized in that the sample comprises glycosylated antibodies and/or viral protein glycoforms.

8. The method according to claim 1, characterized in that the polymer chains are built by monomer units and the monomer units of the polymer chains are linked in a linear manner and each monomer unit comprises an end group —N(Y)—R3.

9. The method according to claim 1, characterized in that Y is H and R4 is isopropyl and/or isobutyl.

10. The method according to claim 1, characterized in that the ionic density of the separation material is between 10-1200 µeq/g.

11. The method according to claim 1, characterized in that the protein glycoforms are bound to the separation material at a pH between 2 and 7, and are washed and eluted by increasing the pH value to a value between 9 and 11.

12. The method according to claim 1, characterized in that between 10 mg and 100 mg of the protein glycoforms are bound per ml of the separation material.

13. The method according to claim 1, characterized in that the sample comprises SARS-CoV-2 protein glycoforms.

* * * * *